(12) United States Patent
Alarcon Sanchez et al.

(10) Patent No.: US 9,120,764 B2
(45) Date of Patent: Sep. 1, 2015

(54) CHROMENE DERIVATIVES

(75) Inventors: Balbino Jose Alarcon Sanchez, Madrid (ES); Angel Messeguer Peypoch, Barcelona (ES); Antonio Morreale De Leon, Madrid (ES); Aldo Jorge Borroto Revuelta, Madrid (ES); Irene Azahara Arellano Rojo, Madrid (ES); Almudena Perona Requena, Madrid (ES); Esther Carrasco Romero, Barcelona (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 203 days.

(21) Appl. No.: 13/824,178

(22) PCT Filed: Jul. 8, 2011

(86) PCT No.: PCT/ES2011/070506
§ 371 (c)(1),
(2), (4) Date: Sep. 12, 2013

(87) PCT Pub. No.: WO2012/042078
PCT Pub. Date: Apr. 5, 2012

(65) Prior Publication Data
US 2014/0005247 A1 Jan. 2, 2014

(30) Foreign Application Priority Data
Sep. 28, 2010 (ES) .................. 201031437

(51) Int. Cl.
*C07D 405/06* (2006.01)
*A61K 31/4025* (2006.01)
*C07D 295/084* (2006.01)
*C07D 311/58* (2006.01)
*C07D 405/14* (2006.01)

(52) U.S. Cl.
CPC ........ *C07D 295/084* (2013.01); *A61K 31/4025* (2013.01); *C07D 311/58* (2013.01); *C07D 405/06* (2013.01); *C07D 405/14* (2013.01)

(58) Field of Classification Search
CPC .......................... C07D 405/06; A61K 31/4025
USPC ........................................... 548/525; 514/422
See application file for complete search history.

(56) References Cited

FOREIGN PATENT DOCUMENTS

WO    WO 2010064707    *    6/2010    ........... C07D 403/12

OTHER PUBLICATIONS

Kaur et al. (European Journal of Pharmaceutical Sciences 47 (2012) 574-588).*
Das et al. (Bioorg. Med. Chem. Lett. 16 (2006) 3706-3712).*
Kubinyi (3D QSAR in Drug Design: Ligand-Protein Interactions and Molecular Similarity, vol. 2-3, Springer, 1998, 800 pages). pp. 243-44 provided.*
Wermuth, The Practice of Medicinal Chemsitry, 2d ed. (2003), 768 pages. Chs. 9-10 provided.*
Vogel's Textbook of Practical Organic Chemistry, 5th ed. (1989), 1514 pages). pp. 989-999 provided.*

* cited by examiner

*Primary Examiner* — Robert Havlin
(74) *Attorney, Agent, or Firm* — McNees Wallace & Nurick LLC

(57) ABSTRACT

Derivates of chromene of formula I, where the meanings for the various substituents are as indicated in the description. These compounds are useful as inhibitors of TCR-Nck interaction in T lymphocytes.

10 Claims, 3 Drawing Sheets

CHROMENE DERIVATIVES

The present invention relates to a new series of chromene derivates as well as processes for their preparation, pharmaceutical compositions comprising these compounds and their use in therapy.

STATE OF THE ART

T lymphocytes play a central role in transplant rejection and, in a more or less direct way, in the generation of the autoimmune diseases. Therefore, current immunosuppressive drugs mechanisms of action are based on the inhibition of T lymphocyte activation. These immunosuppressants have highly toxic profiles, since they do not inhibit specific pathways for lymphocyte activation. T lymphocytes are activated through the antigen receptor (TCR) which recognizes the major histocompatibility complex (MHC) of the transplanted organ as foreign. The TCR is formed by six subunits, two of which (TCRα and TCRβ) are responsible for the recognition of the MHC bound to antigen peptides while the other four (CD3γ, CD3δ, CD3ε and CD3ζ) are responsible for signal transduction to the lymphocyte cytoplasm (reviewed in Alarcon, B., Gil, D., Delgado, P. and Schamel, W. W. (2003) *Immunol Rev,* 191, 38-46). One of the initial processes that occur after binding of TCR by MHC is the activation of the tyrosine kinases of the src family, Lck and Fyn, which phosphorylate the tyrosines of the ITAM motifs of the CD3 subunits, which in turn become sites of anchorage of the tyrosines kinases of the Syk family (ZAP70 and Syk). Until recently it was thought that this was the linear scheme for signal transduction and that, from the kinases of the Syk family (ZAP70 mostly), a diverging activation cascade occurred resulting in the activation of various transcription factors, including NFAT, the target of the immunosuppressive drugs cyclosporine A and FK506 (Lin, J. and Weiss, A. (2001) *J Cell Sci,* 114, 243-244). Some years ago, the authors of the present invention discovered that, in order to be activated, the TCR undergoes a conformational change that results in the recruitment of the Nck adaptor directly to a proline-rich sequence (PRS) of the CD3ε subunit (Gil, D., Schemel, W. W., Montoya, M., Sanchez-Madrid, F. and Alarcon, B. (2002) *Cell,* 109, 901-912). This TCR-Nck interaction was shown to be essential for TCR activation by experiments involving the over-expression of the amino-terminal SH3.1 domain of Nck (which binds to CD3ε) and by the introduction of the APA1/1 antibody in T lymphocytes, which binds to PRS and blocks it. On the other hand, it has recently been described that Nck is necessary for T lymphocyte activation in response to stimulation of the TCR (Roy, E., Togbe, D., Holdorf, A. D., Trubetskoy, D., Nabti, D., Küblbeck, G., Klevenz, A., Kopp-Schneider, A. D., Leithäuser, F., Möller, P., Bladt, F., Hämmerling, G., Arnold, B., Pawson, T., and Tarufi, A. (2010) *Proc Natl Acad Sci USA,* 107, 15529-15534).

Therefore, it would be desirable to provide new compounds which are able to inhibit TCR-Nck interaction in T lymphocytes, and who are good candidates for drugs. Compounds should display a good activity on in vivo pharmacological tests, a good oral absorption when they are administered orally, as well as be metabolically stable, and have a favorable pharmacokinetic profile. In addition, compounds should not be toxic and have limited side effects.

DESCRIPTION OF THE INVENTION

One aspect of the invention relates to compounds of formula I:

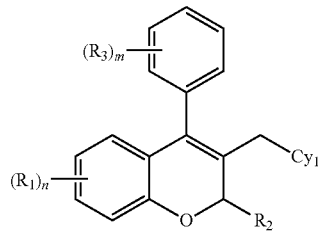

where:

each $R_1$ and $R_3$ independently represent hydrogen, $C_{1-4}$alkyl, $C_{2-4}$ alkenyl, $C_{2-4}$alkynyl, hydroxyl, $C_{1-4}$alkoxyl, $C_{1-4}$alkoxyC$_{1-4}$alkyl, haloC$_{1-4}$alkyl, hydroxyC$_{1-4}$alkyl, cyanoC$_{1-4}$alkyl, halogen, —CN, —NO$_2$ or Cy$_2$;

$R_2$ represents hydrogen, $C_{1-4}$alkyl or Cy$_2$, where C$_{1-4}$alkyl is optionally substituted by Cy$_2$;

Cy$_1$ represents a monocyclic heterocycle of 3 to 7 members or bicyclic from 6 to 11 members, saturated or partially unsaturated which can be joined to the rest of the molecule by any available C or N atom, where Cy$_1$ can be optionally merged to a ring of 5 or 6 members carbocyclic or heterocyclic saturated, partly unsaturated or aromatic, where Cy$_1$ can contain from 1 to 4 heteroatoms selected from N, O and S, where one or more atoms of C or S of the ring may be oxidized to form groups CO, SO or SO$_2$, and where Cy$_1$ is optionally replaced by one or more $R_4$;

each Cy$_2$ independently represents an aromatic ring of 5 to 7 members which can be joined to the rest of the molecule by any C or N available atom, where Cy$_2$ can be optionally merged to a ring of 5 or 6 members carbocyclic or heterocyclic saturated, partly unsaturated or aromatic, where Cy$_2$ can contain from 1 to 4 heteroatoms in total selected from N, O and S, where one or more atoms of C or S of the ring can be oxidized to form groups CO, SO or SO$_2$, and where Cy$_2$ is optionally replaced by one or more $R_4$;

each $R_4$ independently represents, $C_{1-4}$alkyl, $C_{2-4}$alkenyl, $C_{2-4}$alkynyl, hydroxyl, $C_{1-4}$alkoxyl, $C_{1-4}$alkoxyC$_{1-4}$ alkyl, haloC$_{1-4}$alkyl, hydroxyC$_{1-4}$alkyl, cyanoC$_{1-4}$alkyl, halogen, —CN or —NO$_2$;

n represents from 0 to 4; and m represents from 0 to 5.

The present invention further relates to the salts and solvates of compounds of formula I.

Some compounds of formula I may have chiral centers, which can give rise to various stereoisomers. The present invention relates to each of the individual stereoisomer and their mixtures.

The compounds of formula I are inhibitors of TCR-Nck interaction in T lymphocytes and can be used to treat diseases mediated by this interaction TCR-Nck in lymphocytes T.

Thus, another aspect of the invention is concerned to a compound of formula I

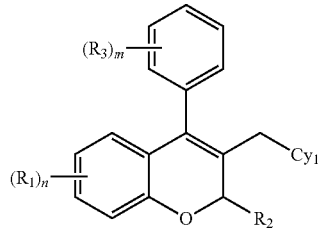

where:
- each $R_1$ and $R_3$ independently represent hydrogen, $C_{1-4}$alkyl, $C_{2-4}$ alkenyl, $C_{2-4}$alkynyl, hydroxyl, $C_{1-4}$alkoxyl, $C_{1-4}$alkoxyC$_{1-4}$alkyl, haloC$_{1-4}$alkyl, hydroxyC$_{1-4}$alkyl, cyanoC$_{1-4}$alkyl, halogen, —CN, —NO$_2$ or Cy$_2$;
- $R_2$ represents hydrogen, $C_{1-4}$alkyl or Cy$_2$, where $C_{1-4}$alkyl is optionally substituted by Cy$_2$;
- Cy$_1$ represents a monocyclic heterocycle of 3 to 7 members or bicyclic from 6 to 11 members, saturated or partially unsaturated which can be joined to the rest of the molecule by any available C or N atom, where Cy$_1$ can be optionally merged to a ring of 5 or 6 members carbocyclic or heterocyclic saturated, partly unsaturated or aromatic, where Cy$_1$ can contain from 1 to 4 heteroatoms selected from N, O and S, where one or more atoms of C or S of the ring may be oxidized to form groups CO, SO or SO$_2$, and where Cy$_1$ is optionally replaced by one or more R$_4$;
- each Cy$_2$ independently represents an aromatic ring of 5 to 7 members which can be joined to the rest of the molecule by any C or N available atom, where Cy$_2$ can be optionally merged to a ring of 5 or 6 members carbocyclic or heterocyclic saturated, partly unsaturated or aromatic, where Cy$_2$ can contain from 1 to 4 heteroatoms in total selected from N, O and S, where one or more atoms of C or S of the ring can be oxidized to form groups CO, SO or SO$_2$, and where Cy$_2$ is optionally replaced by one or more R$_4$;
- each R$_4$ independently represent, $C_{1-4}$alkyl, $C_{2-4}$alkenyl, $C_{2-4}$alkynyl, hydroxyl, $C_{1-4}$alkoxyl, $C_{1-4}$alkoxyC$_{1-4}$alkyl, haloC$_{1-4}$alkyl, hydroxyC$_{1-4}$alkyl, cyanoC$_{1-4}$alkyl, halogen, —CN or —NO$_2$;
- n represents from 0 to 4; and
- m represents from 0 to 5.

to be used in therapy.

Another aspect of the present invention relates to a pharmaceutical composition comprising a compound of formula I or a pharmaceutically acceptable salt thereof and one or more pharmaceutically acceptable excipients.

Another aspect of the present invention relates to use of a compound of formula I or a pharmaceutically acceptable salt thereof for the preparation of a medicament for the treatment of diseases mediated by TCR-Nck interaction in T lymphocytes.

Another aspect of the present invention relates to use of a compound of formula I or a pharmaceutically acceptable salt thereof for the preparation of a medicament for the treatment a disease selected from among transplant rejection, autoimmune diseases, autoimmune or inflammatory diseases, neurodegenerative and proliferative diseases. Preferably, the disease is selected from transplant rejection and autoimmune diseases, inflammatory or autoimmune.

Another aspect of the present invention relates to use of a compound of formula I or a pharmaceutically acceptable salt thereof for the preparation of a medicament for the treatment of a disease selected from among transplant rejection, rheumatoid arthritis, psoriatic arthritis, psoriasis, Type I diabetes, diabetes complications, multiple sclerosis, lupus erythematosus, atopic dermatitis, allergic reactions mediated by mast cell, leukemias, lymphomas and thromboembolic and allergic complications associated a leukemias and lymphomas.

Another aspect of the present invention refers to a process of preparation of a compound of formula I as defined above, comprising:
(a) reacting a compound of formula II with a compound of formula III

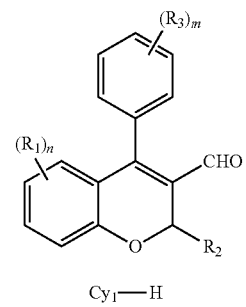

where $R_1$, $R_2$, $R_3$, Cy$_1$, n and m have the meaning described above; and/or
(b) transforming, in one or more steps, a compound of formula I into another compound of formula I.

In the above definitions, the term $C_{1-4}$alkyl, as a group or part of a group, means an alkyl group of linear or branched chain which contains 1 to 4 C atoms and includes groups methyl, ethyl, propyl, isopropyl, butyl, isobutyl, sec-butyl and tert-butyl.

A group $C_{2-4}$alkenyl means a linear or branched alquilic chain that contains 2 to 4 C atoms, and also contains one or two double bonds. Examples include the groups ethenyl, 1-propenyl, 2-propenyl, isopropenyl, 1-butenyl, 2-butenyl, 3-butenyl, and 1,3-butadienyl.

A group $C_{2-4}$alkynyl means a linear or branched alquilic chain that contains from 2 to 4 C atoms, and also contains one or two triple bonds. Examples include the groups ethynyl, 1-propynyl, 2-propynyl, 1-butynyl, 2-butynyl, 3-butynyl, and 1,3-butadiynyl.

A group $C_{1-4}$alkoxyl or $C_{1-4}$alkoxy, as a group or part of a group, means a group —OC$_{1-4}$alkyl, where the part $C_{1-4}$alkyl has the same meaning described above. Examples include methoxy, ethoxy, propoxy, isopropoxy, butoxy, isobutoxy, sec-butoxy and tert-butoxy.

An halogen radical or its abbreviation halo means fluoro, chlorine, bromine, or iodine.

A $C_{1-4}$alkoxyC$_{1-4}$alkyl group means a group resulting from the replacement of one or more atoms of hydrogen from a $C_{1-4}$alkyl group for one or more C$_{1-4}$alkoxy groups as defined above, which can be equal or different. Examples include, among others, the groups methoxymethyl, ethoxymethyl, propoxymethyl, isopropoxymethyl, butoxymethyl, isobutoximetilo, sec-butoxymethyl, tert-butoxymethyl, dimetoxymethyl, 1-metoxyethyl, 2-metoxyethyl, 2-ethoxyethyl, 1,2-diethoxyethyl, 1-butoxyethyl, 3-methoxypropyl, 2-butoxypropyl, 1-methoxy-2-ethoxypropyl, 2-sec-butoxyethyl, 3-tert-butoxypropyl and 4-methoxybutyl.

A group haloC$_{1-4}$alkyl means a group resulting from the replacement of one or more atoms of hydrogen of a C$_{1-4}$alkyl group by one or more halogen atoms (i.e., fluoro, chlorine, bromine or iodine), which may be equal or different. Examples include, among others, the groups trifluoromethyl, fluoromethyl, 1-chloroethyl, 2-chloroethyl, 1-fluoroethyl, 2-fluoroethyl, 2-bromoethyl, 2-yodoethyl, 2,2,2-trifluoroethyl, pentafluoroethyl, 3-fluoropropyl, 3-chloropropyl, 2,2,3,3-tetrafluoropropyl, 2,2,3,3,3-pentafluoropropyl, heptafluoropropyl, 4-fluorobutyl and nonafluorobutyl.

A group hydroxyC$_{1-4}$alkyl means a group resulting from the replacement of one or more hydrogen atoms of a C$_{1-4}$alkyl group by one or more hydroxy groups. Examples include, among others, hydroxymethyl, 1-hydroxyethyl, 2-hydroxyethyl, 1,2-dihydroxyethyl, 3-hydroxypropyl, 2-hydroxypropyl, 1-hydroxypropyl, 2,3-dihydroxypropyl, 4-hydroxybutyl, 3-hydroxybutyl, 2-hydroxybutyl and 1-hydroxybutyl.

A group cyanoC$_{1-4}$alkyl means a group resulting from the replacement of one or more hydrogen atoms of a C$_{1-4}$alkyl group by one or more cyano groups. Examples, include among others, the groups cyanomethyl, dicyanomethyl, 1-cyanoethyl, 2-cyanoethyl, 3-cyanopropyl, 2,3-dicyanopropyl and 4-cyanobutyl.

A group Cy$_1$ refers to a monocyclic heterocycle of 3 to 7 members or bicyclic of 6 to 11 members, saturated or partly unsaturated which can be attached to the rest of the molecule through any available C or N atom. When Cy$_1$ is bicyclic the second ring can be saturated, partly unsaturated or aromatic. Cy$_1$ contains a total of 1 to 4 heteroatoms selected from N, O and S. When Cy$_1$ is a bicyclic ring, it can be formed by two rings fused through two adjacent atoms of C or N or two non-adjacent atoms of C o N forming a ring with bridge, or it can be formed by two rings joined together through a single C atom forming a ring of type spirane. In Cy$_1$ on one or more C or S atoms from any saturated or partially unsaturated ring can be optionally oxidized forming groups CO, SO or SO$_2$. The Group Cy$_1$ may be optionally replaced as indicated in the definition of the formula I, these substituents can be equal or different and can be located in any available position of any of the rings. Examples of groups Cy$_1$ include, among others, azepanyl, aziridinyl, azetidinyl, 1,4-diazepanyl, pyrrolidinyl, imidazolidinyl, isoxazolidinyl, oxazolidinyl, pyrazolidinyl, thiazolidinyl, isothiazolidinyl, imidazolinyl, pyrrolinyl, pyrazolinyl, piperidinyl, homopiperidinyl, morpholinyl, thiomorpholinyl, 1,1-dioxothiomorpholinyl, piperazinyl, homopiperazinyl, 2-oxo-azepanyl, 2-oxo-azetidinyl, 2-oxo-1,4-diazepanyl, 2-oxo-pirrolidinyl, 2-oxo-piperazinyl, 2-oxo-piperidinyl, 3-oxo-piperidinyl, 4-oxo-piperidinyl, 2-oxo-imidazolidinyl, 2-oxo-oxazolidinyl, 2-oxo-1,2-dihydropyridyl, 2-oxo-1,2-dihydropyrazinyl, 2-oxo-1,2-dihydropyrimidinyl, 3-oxo-2,3-dihydropyridazyl, 1,2,3,6-tetrahydropyridinyl, perhydroisoquinolinyl, 1-oxo-1,2-dihydroisoquinolinyl, 4-oxo-3,4-dihydroquinazolinyl, 5-aza-bicycle[2.1.1]hexanyl, 2-aza-bicycle[2.2.1]heptanyl, 6-aza-bicycle[3.2.1]octanyl, octahydro-pyrrolo[1,2-a]pirazinilo, 2H-spiro[benzofuran-3,4'-piperidinyl], 3H-spiro[isobenzofuran-1,4'-piperidinyl], 2,8-diazaspiro[4.5]decan-1-onyl, 2,7-diazaspiro[4.5]decan-1-onyl, 2-aza-bicycle[2.2.1]heptan-6-onyl and 6-aza-bicycle[3.2.1]octan-7-onyl.

A group Cy$_2$ refers to an aromatic ring of 5 to 7 members that can be attached to the rest of the molecule by any C or N available atom. Cy$_2$ can be optionally merged to a 5 or 6 membered ring, the fused ring can be carbocyclic or heterocyclic and can be saturated, partly unsaturated or aromatic. Cy$_2$ can contain from 1 to 4 heteroatoms selected from N, O and S. When Cy$_2$ is a bicyclic ring, it can be formed by two rings fused through two adjacent atoms of C or N, or two non-adjacent atoms of C o N forming a ring with bridge, or it can be formed by two rings joined together through a single C atom forming a ring of type spirane. In Cy$_2$ one or more C or S atoms from any saturated or partially unsaturated ring can be optionally oxidized forming groups CO, SO or SO$_2$. The group Cy$_2$ can be optionally replaced as indicated in the definition of the formula I, these substituents can be equal or different and can be located in any available position of any of the rings. Examples of groups Cy$_2$ include, among others, phenyl, naphthyl, tienilo, furyl, pyrrolyl, thiazolyl, isothiazolyl, oxazolyl, isoxazolyl, imidazolyl, pyrazolyl, 1,2,3-triazolyl, 1,2,4-triazolyl, tetrazolyl, 1,3,4-oxadiazolyl, 1,3,4-thiadiazolyl, 1,2,4-oxadiazolyl, 1,2,4-thiadiazolyl, pyridyl, pyrazinyl, pyrimidinyl, pyridazinyl, benzimidazolyl, benzooxazolyl, benzofuranyl, isobenzofuranyl, indolyl, isoindolyl, benzothiophenyl, benzothiazolyl, quinolinyl, isoquinolinyl, phthalazinyl, quinazolinyl, quinoxalinyl, cinnolinyl, naphthyridinyl, indazolyl, imidazopyridinyl, pyrrolopyridinyl, thienopyridinyl, imidazopyrimidinyl, imidazopyrazinyl, imidazopyridazinyl, pyrazolopyrazinyl, pyazolopyridinyl, pyrazolopyrimidinyl, benzo[1.3]dioxolyl, phthalimidyl, 1-oxo-1,3-dihydroisobenzofuranyl, 1,3-dioxo-1,3-dihydroisobenzofuranyl, 2-oxo-2,3-dihydro-1H-indolyl, 1-oxo-2,3-dihydro-1H-isoindolyl, 1,2,3,4-tetrahydroquinolinyl, 1,2,3,4-tetrahydroisoquinolinyl, 1-oxo-1,2,3,4-tetrahydroisoquinolinyl, 1-oxo-1,2-dihydroisoquinolinyl and 4-oxo-3,4-dihydroquinazolinyl.

In the above definitions of Cy$_1$ and Cy$_2$, when specified examples refer to a bicyclic ring in general terms, all the possible atoms positions are included.

When in the definitions used throughout the present description for cyclic groups, specified examples refer to a radical of a ring in general terms, e.g. pyridyl, thienyl or indolyl, all possible union positions are included, except when a limitation in this regard is indicated on the corresponding group definition. Thus, for example, definitions of Cy$_1$ and Cy$_2$, which do not include any limitation with respect to the union position, the term imidazolidinyl includes 2-imidazolidinyl and 3-imidazolidinyl.

The expression "optionally substituted by one or more" means the ability of a group to be replaced by one or more, preferably by 1, 2, 3 or 4 substituents, more preferably by 1, 2 or 3 substituents and even more preferably by 1 or 2 substituents, provided that the group has enough available positions likely to be replaced. If they are present, these substituents can be equal or different and can be located on any available position.

When a non-aromatic cycle is a substitute of a non-aromatic cycle, this can be replacing a hydrogen atom, or can replace two hydrogen atoms on the same C atom thus forming a ring of type spirane. Similarly, when a non-aromatic cycle is a substitute of an alkyl, alkenyl, or alkinyl group, it can be replacing a hydrogen atom, or can replace two hydrogen atoms of the same C atom.

Throughout this description, the expressions "treatment" of a disease, "treat" a disease or other grammatically related expressions refer to curative treatment, palliative treatment or prophylactic treatment of the disease.

The invention therefore refers to the compounds of formula I as defined above.

In another embodiment, the invention refers to the compounds of formula I where every R$_1$ and R$_3$ independently represent hydrogen, C$_{1-4}$alkyl, hydroxyl, C$_{1-4}$alkoxyl C$_{1-4}$alkoxyC$_{1-4}$alkyl, haloC$_{1-4}$alkyl, hydroxyC$_{1-4}$alkyl, cyanoC$_{1-4}$alkyl, halogen, —CN, or Cy$_2$.

In another embodiment, the invention refers to the compounds of formula I where every $R_1$ and $R_3$ independently represents hydrogen, $C_{1-4}$alkyl, halo$C_{1-4}$alkyl, $C_{1-4}$alkoxyl, halogen or $Cy_2$.

In another embodiment, the invention refers to the compounds of formula I where each $R_1$ independently represents hydrogen, $C_{1-4}$alkoxyl or $Cy_2$.

In another embodiment, the invention refers to the compounds of formula I where each $R_3$ independently represents $C_{1-4}$alkyl, halo$C_{1-4}$alkyl or halogen, preferably halo$C_{1-4}$alkyl or halogen.

In another embodiment, the invention refers to the compounds of formula I where $R_2$ represents hydrogen.

In another embodiment, the invention refers to the compounds of formula I where:
  each $R_1$ and $R_3$ independently represent hydrogen, $C_{1-4}$alkyl, halo$C_{1-4}$alkyl, $C_{1-4}$alkoxyl, halogen or $Cy_2$; and
  $R_2$ represents hydrogen.

In another embodiment, the invention refers to the compounds of formula I where:
  each $R_1$ independently represents hydrogen, $C_{1-4}$alkoxyl or $Cy_2$; and
  $R_2$ represents hydrogen.

In another embodiment, the invention refers to the compounds of formula I where:
  each $R_3$ independently represents $C_{1-4}$alkyl, halo$C_{1-4}$alkyl or halogen, preferably halo$C_{1-4}$alkyl or halogen; and
  $R_2$ represents hydrogen.

In another embodiment, the invention refers to the compounds of formula I where:
  each $R_1$ independently represents hydrogen, $C_{1-4}$alkoxyl or $Cy_1$;
  each $R_3$ independently represents $C_{1-4}$alkyl, halo$C_{1-4}$alkyl or halogen, preferably halo$C_{1-4}$alkyl or halogen; and
  $R_2$ represents hydrogen.

In another embodiment, the invention refers to the compounds of formula I where $Cy_1$ represents a monocyclic heterocycle of 3 to 7 members, saturated or partially unsaturated which can be attached to the rest of the molecule by any available C o N atom, where $Cy_1$ can contain from 1 to 3 heteroatoms selected from N, O and S, where one or more C or S atoms of the ring can be oxidized to form groups CO, SO or $SO_2$, and where $Cy_1$ is optionally replaced by one or more $R_3$.

In another embodiment, the invention refers to the compounds of formula I where $Cy_1$ represents a monocyclic heterocycle of 5 or 6 members, saturated or partially unsaturated which can be attached to the rest of the molecule by any available C or N atom, where $Cy_1$ can contain from 1 to 3 heteroatoms selected from N, O and S, where one or more C or S atoms of the ring can be oxidized to form groups CO, SO or $SO_2$, and where $Cy_1$ is optionally replaced by one or more $R_4$.

In another embodiment, the invention refers to the compounds of formula I where $Cy_1$ represents a monocyclic heterocycle of 5 or 6 members, saturated or partially unsaturated which can be joined to the rest of the molecule by any available C or N atom, where $Cy_1$ can contain from 1 to 3 heteroatoms selected from N, O and S, where one or more C or S atoms of the ring can be oxidized to form groups CO, SO or $SO_2$, and where $Cy_1$ is optionally replaced by one or more $R_4$.

In another embodiment, the invention refers to the compounds of formula I where $Cy_1$ represents a monocyclic heterocycle of 5 or 6 members, saturated or partially unsaturated which is joined to the rest of the molecule by any available N atom, where $Cy_1$ can contain 1 or 2 heteroatoms selected from N, O and S, where one or more C or S atoms of the ring can be oxidized to form groups CO, SO or $SO_2$, and where $Cy_1$ is optionally replaced by one or more $R_4$.

In another embodiment, the invention refers to the compounds of formula I where $Cy_1$ represents the group:

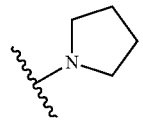

where $Cy_1$ is optionally replaced by one or more $R_4$.

In another embodiment, the invention refers to the compounds of formula I where $Cy_1$ represents the group:

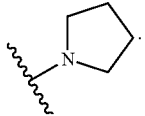 [SMILES: *N1CCCC1]

In another embodiment, the invention refers to the compounds of formula I where:
  each $R_1$ and $R_3$ independently represent hydrogen, $C_{1-4}$alkyl, halo$C_{1-4}$alkyl, $C_{1-4}$alkoxyl, halogen or $Cy_1$;
  $R_2$ represents hydrogen; and
  $Cy_1$ represents a monocyclic heterocycle of 5 to 6 members, saturated or partially unsaturated which is joined to the rest of the molecule by any available N atom, where $Cy_1$ can contain 1 or 2 heteroatoms selected from N, O and S, where one or more atoms of C or S of the ring can be oxidized to form groups CO, SO or $SO_2$, and where $Cy_1$ is optionally replaced by one or more $R_4$.

In another embodiment, the invention refers to the compounds of formula I where:
  each $R_1$ independently represent hydrogen, $C_{1-4}$alkoxyl or $Cy_2$;
  $R_2$ represents hydrogen; and
  $Cy_1$ represents a monocyclic heterocycle of 5 or 6 members, saturated or partially unsaturated which is joined to the rest of the molecule by any available N Atom, where $Cy_1$ can contain 1 or 2 heteroatoms selected from N, O and S, where one or more C or S atoms of the ring can be oxidized to form groups CO, SO or $SO_2$, and where $Cy_1$ is optionally replaced by one or more $R_4$.

In another embodiment, the invention refers to the compounds of formula I where:
  each $R_3$ independently represent $C_{1-4}$alkyl, halo$C_{1-4}$alkyl or halogen, preferably halo$C_{1-4}$alkyl or halogen;
  $R_2$ represents hydrogen; and
  $Cy_1$ represents a monocyclic heterocycle of 5 or 6 members, saturated or partially unsaturated which is joined to the rest of the molecule by any available N atom, where $Cy_1$ can contain 1 or 2 heteroatoms selected from N, O and S, where one or more atoms of C or S of the ring can be oxidized to form groups CO, SO or $SO_2$, and where $Cy_1$ is optionally replaced by one or more $R_4$.

In another embodiment, the invention refers to the compounds of formula I where:
  each $R_1$ independently represents hydrogen, $C_{1-4}$alkoxyl or $Cy_2$;
  each $R_3$ independently represents $C_{1-4}$alkyl, halo$C_{1-4}$alkyl or halogen, preferably halo$C_{1-4}$alkyl or halogen;

$R_2$ represents hydrogen; and $Cy_1$ represents a monocyclic heterocycle of 5 to 6 members, saturated or partially unsaturated which is joined to the rest of the molecule by any available N atom, where $Cy_1$ can contain 1 or 2 heteroatoms selected from N, O and S, where one or more atoms of C or S of the ring may be oxidized to form groups CO, SO or $SO_2$, and where $Cy_1$ is optionally replaced by one or more $R_4$.

In another embodiment, the invention refers to the compounds of formula I where:

each $R_1$ and $R_3$ independently represent hydrogen, $C_{1-4}$alkyl, halo$C_{1-4}$alkyl, $C_{1-4}$alkoxyl, halogen or $Cy_2$;

$R_2$ represents hydrogen; and $Cy_1$ represents the group:

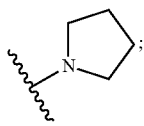

where $Cy_1$ is optionally replaced by one or more $R_4$

In another embodiment, the invention refers to the compounds of formula I where:

each $R_1$ independently represents hydrogen, $C_{1-4}$alkoxyl or $Cy_2$;

$R_2$ represents hydrogen; and $Cy_1$ represents the group:

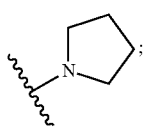

where $Cy_1$ is optionally replaced by one or more $R_4$.

In another embodiment, the invention refers to the compounds of formula I where:

each $R_3$ independently represents $C_{1-4}$alkyl, halo$C_{1-4}$alkyl or halogen, preferably halo$C_{1-4}$alkyl or halogen;

$R_2$ represents hydrogen; and.

$Cy_1$ represents the group:

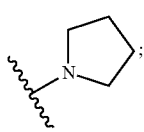

where $Cy_1$ is optionally replaced by one or more $R_4$.

In another embodiment, the invention refers to the compounds of formula I where:

each $R_1$ independently represents hydrogen, $C_{1-4}$alkoxyl or $Cy_2$;

each $R_3$ independently represents $C_{1-4}$alkyl, halo$C_{1-4}$alkyl or halogen, preferably halo$C_{1-4}$alqkyl or halogen;

$R_2$ represents hydrogen; and $Cy_1$ represents the group:

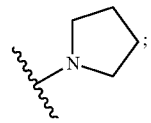

where $Cy_1$ is optionally replaced by one or more $R_4$.

In another embodiment, the invention refers to the compounds of formula I where each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO or $SO_2$, and where $Cy_2$ is optionally replaced by one or more $R_4$.

In another embodiment, the invention refers to the compounds of formula I where:

each $R_1$ and $R_3$ independently represent hydrogen, $C_{1-4}$alkyl, halo$C_{1-4}$alkyl, $C_{1-4}$alkoxyl, halogen or $Cy_2$;

$R_2$ represents hydrogen; and each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO or $SO_2$, and where $Cy_2$ is optionally replaced by one or more $R_4$.

In another embodiment, the invention refers to the compounds of formula I where:

each $R_1$ independently represents hydrogen, $C_{1-4}$alkoxyl or $Cy_2$;

$R_2$ represents hydrogen; and each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO or $SO_2$, and where $Cy_2$ is optionally replaced by one or more $R_4$.

In another embodiment, the invention refers to the compounds of formula I where:

each $R_3$ independently represents $C_{1-4}$alkyl, halo$C_{1-4}$alkyl or halogen, preferably halo$C_{1-4}$alkyl or halogen;

$R_2$ represents hydrogen; and each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO or $SO_2$, and where $Cy_2$ is optionally replaced by one or more $R_4$ In another embodiment, the invention refers to the compounds of formula I where:

each $R_1$ independently represents hydrogen, $C_{1-4}$alkoxyl or $Cy_2$;

each $R_3$ independently represents $C_{1-4}$alkyl, halo$C_{1-4}$alkyl or halogen, preferably halo$C_{1-4}$alkyl or halogen;

$R_2$ represents hydrogen; and each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO or $SO_2$, and where $Cy_2$ is optionally replaced by one or more $R_4$.

In another embodiment, the invention refers to the compounds of formula I where:
  each $R_1$ independently represents hydrogen, $C_{1-4}$alkoxyl or $Cy_2$;
  $R_2$ represents hydrogen;
  $Cy_1$ represents a monocyclic heterocyclic of 5 or 6 members, saturated or partially unsaturated which is attached to the rest of the molecule by any available N atom, where $Cy_1$ may contain 1 or 2 heteroatoms selected from N, O and S, where one or more C or S atoms of the ring can be oxidized to form groups CO, SO or $SO_2$, and where $Cy_1$ is optionally replaced by one or more $R_4$; and
  each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more C or S atoms of the ring can be oxidized to form groups CO, SO or $SO_2$, and where $Cy_2$ is optionally replaced by one or more $R_4$.

In another embodiment, the invention refers to the compounds of formula I where:
  each $R_3$ independently represents $C_{1-4}$alkyl, halo$C_{1-4}$alkyl or halogen, preferably halo$C_{1-4}$alkyl or halogen;
  $R_2$ represents hydrogen;
  $Cy_1$ represents a monocyclic heterocycle of 5 or 6 members, saturated or partially unsaturated which is attached to the rest of the molecule by any available N atom, where $Cy_1$ can contain 1 or 2 heteroatoms selected from N, O and S, where one or more C or S atoms of the ring can be oxidized to form groups CO, SO or $SO_2$, and where $Cy_1$ is optionally replaced by one or more $R_4$; and
  each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO or $SO_2$, and where $Cy_2$ is optionally replaced by one or more $R_4$.

In another embodiment, the invention refers to the compounds of formula I where:
  each $R_1$ independently represents hydrogen, $C_{1-4}$alkoxyl or $Cy_2$;
  each $R_3$ independently represents $C_{1-4}$alkyl, halo$C_{1-4}$alkyl or halogen, preferably halo$C_{1-4}$alkyl or halogen;
  $R_2$ represents hydrogen;
  $Cy_1$ represents a monocyclic heterocycle of 5 or 6 members, saturated or partially unsaturated which is attached to the rest of the molecule by any available N atom, where $Cy_1$ can contain 1 or 2 heteroatoms selected from N, O and S, where one or more C or S atoms of the ring can be oxidized to form groups CO, SO or $SO_2$, and where $Cy_1$ is optionally replaced by one or more $R_4$; and
  each $Cy_2$ independently represents phenyl or an aromatic ring of 5 or 6 members which can be attached to the rest of the molecule by any available C or N atom, where $Cy_2$ contains 1 or heteroatoms selected from N, O and S, where one or more atoms of C or S of the ring may be oxidized to form groups CO, SO or $SO_2$, and where $Cy_2$ is optionally replaced by one or more $R_4$.

In another embodiment, the invention refers to the compounds of formula I where:
  each $R_1$ independently represents hydrogen, $C_{1-4}$alkoxyl or $Cy_2$;
  $R_2$ represents hydrogen;
  $Cy_1$ represents the group:

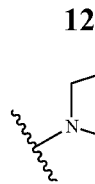

where $Cy_1$ is optionally replaced by one or more $R_4$; and
each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO or $SO_2$, and where $Cy_2$ is optionally replaced by one or more $R_4$.

In another embodiment, the invention refers to the compounds of formula I where:
  each $R_3$ independently represents $C_{1-4}$alkyl, halo$C_{1-4}$alkyl or halogen, preferably halo$C_{1-4}$alkyl or halogen;
  $R_2$ represents hydrogen;
  $Cy_1$ represents the group:

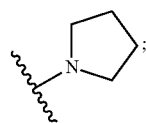

where $Cy_1$ is optionally replaced by one or more $R_4$; and
each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO or $SO_2$, and where $Cy_2$ is optionally replaced by one or more $R_4$.

In another embodiment, the invention refers to the compounds of formula I where:
  each $R_1$ independently represents hydrogen, $C_{1-4}$alkoxyl or $Cy_2$;
  each $R_3$, $R_1$ independently represents $C_{1-4}$alkyl, halo$C_{1-4}$alkyl or halogen, preferably halo$C_{1-4}$alkyl or halogen;
  $R_2$ represents hydrogen;
  $Cy_1$ represents the group:

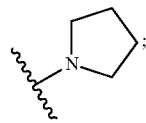

where $Cy_1$ is optionally replaced by one or more $R_4$; and
each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO o $SO_2$, and where $Cy_2$ is optionally replaced by one or more $R_4$.

In another embodiment, the invention refers to the compounds of formula I where each $R_4$ independently represents $C_{1-4}$alkyl, hydroxyl, $C_{1-4}$alkoxyl, $C_{1-4}$alkoxy$C_{1-4}$alquilo, hydroxy$C_{1-4}$alkyl, cyano$C_{1-4}$alkyl, halogen, or —CN.

In another embodiment, the invention refers to the compounds of formula I where each $R_4$ independently represents $C_{1-4}$alkyl, hydroxyl, $C_{1-4}$alkoxyl, halo$C_{1-4}$alkyl, hydroxy$C_{1-4}$ alkyl or halogen.

In another embodiment, the invention refers to the compounds of formula I where:
- each $R_1$ and $R_3$ independently represent hydrogen, $C_{1-4}$alkyl, halo$C_{1-4}$alkyl, $C_{1-4}$alkoxyl, halogen or $Cy_2$;
- $R_2$ represents hydrogen;
- each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO or $SO_2$, and where $Cy_2$ is optionally replaced by one or more $R_4$; and
- each $R_4$ independently represents $C_{1-4}$alkyl, hydroxyl, $C_{1-4}$alkoxyl, halo$C_{1-4}$alkyl, hydroxy$C_{1-4}$alkyl or halogen.

In another embodiment, the invention refers to the compounds of formula I where:
- each $R_1$ independently represents hydrogen, $C_{1-4}$alkoxyl or $Cy_2$;
- $R_2$ represents hydrogen;
- each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO o $SO_2$, and where $Cy_2$ is optionally replaced by one or more $R_4$; and
- each $R_4$ independently represents $C_{1-4}$alkyl, hydroxyl, $C_{1-4}$alkoxyl, halo$C_{1-4}$alkyl, hydroxy$C_{1-4}$alkyl or halogen.

In another embodiment, the invention refers to the compounds of formula I where:
- each $R_3$ independently represents $C_{1-4}$alkyl, halo$C_{1-4}$alkyl or halogen, preferably halo$C_{1-4}$alkyl or halogen;
- $R_2$ represents hydrogen;
- each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO or $SO_2$, and where $Cy_2$ is optionally replaced by one or more $R_4$; and
- each $R_4$ independently represents $C_{1-4}$alkyl, hydroxyl, $C_{1-4}$alkoxyl, halo$C_{1-4}$alkyl, hydroxy$C_{1-4}$alkyl or halogen.

In another embodiment, the invention refers to the compounds of formula I where:
- each $R_1$ independently represents hydrogen, $C_{1-4}$alkoxyl or $Cy_2$;
- each $R_3$ independently represents $C_{1-4}$alkyl, halo$C_{1-4}$alkyl or halogen, preferably halo$C_{1-4}$alkyl or halogen;
- $R_2$ represents hydrogen;
- each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO or $SO_2$, and where $Cy_2$ is optionally replaced by one or more $R_4$; and
- each $R_4$ independently represents $C_{1-4}$alkyl, hydroxyl, $C_{1-4}$alkoxyl, halo$C_{1-4}$alkyl, hydroxy$C_{1-4}$alkyl or halogen.

In another embodiment, the invention refers to the compounds of formula I where:
- each $R_1$ independently represents hydrogen, $C_{1-4}$alkoxyl or $Cy_2$;
- $R_2$ represents hydrogen;
- $Cy_1$ represents a monocyclic heterocycle of 5 or 6 members, saturated or partially unsaturated which is joined to the rest of the molecule by any available N atom, where $Cy_1$ can contain 1 or 2 heteroatoms selected from N, O and S, where one or more atoms of C or S of the ring may be oxidized to form groups CO, SO or $SO_2$, and where $Cy_1$ is optionally replaced by one or more $R_4$;
- each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO or $SO_2$, and where $Cy_2$ is optionally replaced by one or more $R_4$; and
- each $R_4$ independently represents $C_{1-4}$alkyl, hydroxyl, $C_{1-4}$alkoxyl, halo$C_{1-4}$alkyl, hydroxy$C_{1-4}$alkyl or halogen.

In another embodiment, the invention refers to the compounds of formula I where:
- each $R_3$ independently represents $C_{1-4}$alkyl, halo$C_{1-4}$alkyl or halogen, preferably halo$C_{1-4}$alkyl or halogen;
- $R_2$ represents hydrogen;
- $Cy_1$ represents a monocyclic heterocycle of 5 or 6 members, saturated or partially unsaturated which is joined to the rest of the molecule by any available N atom, where $Cy_1$ can contain 1 or 2 heteroatoms selected from N, O and S, where one or more atoms of C or S of the ring may be oxidized to form groups CO, SO or $SO_2$, and where $Cy_1$ is optionally replaced by one or more $R_4$;
- each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO or $SO_2$, and where $Cy_2$ is optionally replaced by one or more $R_4$; and
- each $R_4$ independently represents $C_{1-4}$alkyl, hydroxyl, $C_{1-4}$alkoxyl, halo$C_{1-4}$alkyl, hydroxy$C_{1-4}$alkyl or halogen.

In another embodiment, the invention refers to the compounds of formula I where:
- each $R_1$ independently represents hydrogen, $C_{1-4}$alkoxyl or $Cy_2$;
- each $R_3$ independently represents $C_{1-4}$alkyl, halo$C_{1-4}$alkyl or halogen, preferably halo$C_{1-4}$alkyl or halogen;
- $R_2$ represents hydrogen;
- $Cy_1$ represents a monocyclic heterocycle of 5 or 6 members, saturated or partially unsaturated which is joined to the rest of the molecule by any available N atom, where $Cy_1$ can contain 1 or 2 heteroatoms selected from N, O and S, where one or more atoms of C or S of the ring may be oxidized to form groups CO, SO or $SO_2$, and where $Cy_1$ is optionally replaced by one or more $R_4$;
- each $Cy_2$ independently represents phenyl or an aromatic ring of 5 or 6 members which can be attached to the rest of the molecule by any available C or N atom, where $Cy_2$ contain 1 or 2 heteroatoms selected from N, O and S, where one or more atoms of C or S of the ring may be oxidized to form groups CO, SO or $SO_2$, and where $Cy_2$ is optionally replaced by one or more $R_4$; and each $R_4$ independently represents $C_{1-4}$alkyl, hydroxyl, $C_{1-4}$alkoxyl, halo$C_{1-4}$alkyl, hydroxy$C_{1-4}$alkyl or halogen.

In another embodiment, the invention refers to the compounds of formula I where:

each $R_1$ independently represents hydrogen, $C_{1-4}$alkoxyl or $Cy_2$;

$R_2$ represents hydrogen;

$Cy_1$ represents the group:

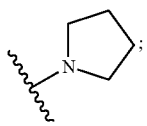

where $Cy_1$ is optionally replaced by one or more $R_4$;

each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO or $SO_2$, and where $Cy_2$ is optionally replaced by one or more $R_4$; and each $R_4$ independently represents $C_{1-4}$alkyl, hydroxyl, $C_{1-4}$alkoxyl, halo$C_{1-4}$alkyl, hydroxy$C_{1-4}$alkyl or halogen.

In another embodiment, the invention refers to the compounds of formula I where:

each $R_3$ independently represents $C_{1-4}$alkyl, halo$C_{1-4}$alkyl or halogen, preferably halo$C_{1-4}$alkyl or halogen;

$R_2$ represents hydrogen;

$Cy_1$ represents the group:

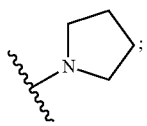

where $Cy_1$ is optionally replaced by one or more $R_4$;

each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO or $SO_2$, and where $Cy_2$ is optionally replaced by one or more $R_4$; and each $R_4$ independently represents $C_{1-4}$alkyl, hydroxyl, $C_{1-4}$alkoxyl, halo$C_{1-4}$alkyl, hydroxy$C_{1-4}$alkyl or halogen.

In another embodiment, the invention refers to the compounds of formula I where:

each independently represents hydrogen, $C_{1-4}$alkoxyl or $Cy_2$;

each $R_3$ independently represents $C_{1-4}$alkyl, halo$C_{1-4}$alkyl or halogen, preferably halo$C_{1-4}$alkyl or halogen;

$R_2$ represents hydrogen;

$Cy_1$ represents the group:

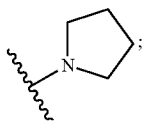

where $Cy_1$ is optionally replaced by one or more $R_4$;

each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO or $SO_2$, and where $Cy_2$ is optionally replaced by one or more $R_4$; and each $R_4$ independently represents $C_{1-4}$alkyl, hydroxyl, $C_{1-4}$alkoxyl, halo$C_{1-4}$alkyl, hydroxy$C_{1-4}$alkyl or halogen.

In another embodiment, the invention refers to the compounds of formula I where n represent from 0 to 2.

In another embodiment, the invention refers to the compounds of formula I where n represents 0 or 1.

In another embodiment, the invention refers to the compounds of formula I where:

each $R_1$ and $R_3$ independently represent hydrogen, $C_{1-4}$alkyl, halo$C_{1-4}$alkyl, $C_{1-4}$alkoxyl, halogen or $Cy_2$;

$R_2$ represents hydrogen;

each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO or $SO_2$, and where $Cy_2$ is optionally replaced by one or more $R_4$;

each $R_4$ independently represents $C_{1-4}$alkyl, hydroxyl, $C_{1-4}$alkoxyl, halo$C_{1-4}$alkyl, hydroxy$C_{1-4}$alkyl or halogen; and n represents 0 or 1.

In another embodiment, the invention refers to the compounds of formula I where:

each $R_1$ independently represents hydrogen, $C_{1-4}$alkoxyl or $Cy_2$;

$R_2$ represents hydrogen;

each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO or $SO_2$, and where $Cy_2$ is optionally replaced by one or more $R_4$;

each $R_4$ independently represents $C_{1-4}$alkyl, hydroxyl, $C_{1-4}$alkoxyl, halo$C_{1-4}$alkyl, hydroxy$C_{1-4}$alkyl or halogen; and n represent 0 or 1.

In another embodiment, the invention refers to the compounds of formula I where:

each $R_3$ independently represents $C_{1-4}$alkyl, halo$C_{1-4}$alkyl or halogen, preferably halo$C_{1-4}$alkyl or halogen;

$R_2$ represents hydrogen;

each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO or $SO_2$, and where $Cy_2$ is optionally replaced by one or more $R_4$;

each $R_4$ independently represents $C_{1-4}$alkyl, hydroxyl, $C_{1-4}$alkoxyl, halo$C_{1-4}$alkyl, hydroxy$C_{1-4}$alkyl or halogen; and n represents 0 or 1.

In another embodiment, the invention refers to the compounds of formula I where:

each $R_1$ independently represents hydrogen, $C_{1-4}$alkoxyl or $Cy_2$;

each $R_3$ independently represents $C_{1-4}$alkyl, halo$C_{1-4}$alkyl or halogen, preferably halo$C_{1-4}$alkyl or halogen;

$R_2$ represents hydrogen;

each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO o $SO_2$, and where $Cy_2$ is optionally replaced by one or more $R_4$;

each $R_4$ independently represents $C_{1-4}$alkyl, hydroxyl, $C_{1-4}$alkoxyl, halo$C_{1-4}$alkyl, hydroxy$C_{1-4}$alkyl or halogen; and n represents 0 or 1.

In another embodiment, the invention refers to the compounds of formula I where:

each $R_1$ independently represents hydrogen, $C_{1-4}$alkoxyl or $Cy_2$;

$R_2$ represents hydrogen;

$Cy_1$ represents a monocyclic heterocycle of 5 or 6 members, saturated or partially unsaturated which is attached to the rest of the molecule by any available N atom, where $Cy_1$ can contain 1 or 2 heteroatoms selected from N, O and S, where one or more C or S atoms of the ring may be oxidized to form groups CO, SO or $SO_2$, and where $Cy_1$ is optionally replaced by one or more $R_4$;

each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO o $SO_2$, and where $Cy_2$ is optionally replaced by one or more $R_4$;

each $R_4$ independently represents $C_{1-4}$alkyl, hydroxyl, $C_{1-4}$alkoxyl, halo$C_{1-4}$alkyl, hydroxy$C_{1-4}$alkyl or halogen; and n represents 0 or 1.

In another embodiment, the invention refers to the compounds of formula I where:

each $R_3$ independently represents $C_{1-4}$alkyl, halo$C_{1-4}$alkyl or halogen, preferably halo$C_{1-4}$alkyl or halogen;

$R_2$ represents hydrogen;

$Cy_1$ represents a monocyclic heterocycle of 5 or 6 members, saturated or partially unsaturated which is attached to the rest of the molecule by any available N atom, where $Cy_1$ can contain 1 or 2 heteroatoms selected from N, O and S, where one or more C or S atoms of the ring may be oxidized to form groups CO, SO or $SO_2$, and where $Cy_1$ is optionally replaced by one or more $R_4$;

each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring can be oxidized to form groups CO, SO or $SO_2$, and where $Cy_2$ is optionally replaced by one or more $R_4$;

each $R_4$ independently represents $C_{1-4}$alkyl, hydroxyl, $C_{1-4}$alkoxyl, halo$C_{1-4}$alkyl, hydroxy$C_{1-4}$alkyl or halogen; and n represents 0 or 1.

In another embodiment, the invention refers to the compounds of formula I where:

each $R_1$ independently represents hydrogen, $C_{1-4}$alkoxyl or $Cy_2$;

each $R_3$ independently represents $C_{1-4}$alkyl, halo$C_{1-4}$alkyl or halogen, preferably halo$C_{1-4}$alkyl or halogen;

$R_2$ represents hydrogen;

$Cy_1$ represents a monocyclic heterocycle of 5 or 6 members, saturated or partially unsaturated which is attached to the rest of the molecule by any available N atom, where $Cy_1$ can contain 1 or 2 heteroatoms selected from N, O and S, where one or more C or S atoms of the ring may be oxidized to form groups CO, SO or $SO_2$, and where $Cy_1$ is optionally replaced by one or more $R_4$;

each $Cy_2$ independently represents phenyl or an aromatic ring of 5 or 6 members which can be attached to the rest of the molecule by any available C or N atom, where $Cy_2$ contain 1 or 2 heteroatoms selected from N, O and S, where one or more atoms of C or S of the ring may be oxidized to form groups CO, SO o $SO_2$, and where $Cy_2$ is optionally replaced by one or more $R_4$;

each $R_4$ independently represents $C_{1-4}$alkyl, hydroxyl, $C_{1-4}$alkoxyl, halo$C_{1-4}$alkyl, hydroxy$C_{1-4}$alkyl or halogen; and n represents 0 or 1.

In another embodiment, the invention refers to the compounds of formula I where:

each $R_1$ independently represents hydrogen, $C_{1-4}$alkoxyl or $Cy_2$;

$R_2$ represents hydrogen;

$Cy_1$ represents the group:

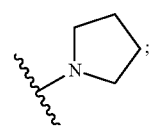

where $Cy_1$ is optionally replaced by one or more $R_4$;

each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring can be oxidized to form groups CO, SO or $SO_2$, and where $Cy_2$ is optionally replaced by one or more $R_4$;

each $R_4$ independently represents $C_{1-4}$alkyl, hydroxyl, $C_{1-4}$alkoxyl, halo$C_{1-4}$alkyl, hydroxy$C_{1-4}$alkyl or halogen; and n represents 0 or 1.

In another embodiment, the invention refers to the compounds of formula I where:

each $R_3$ independently represents $C_{1-4}$alkyl, halo$C_{1-4}$alkyl or halogen, preferably halo$C_{1-4}$alkyl or halogen;

$R_2$ represents hydrogen;

$Cy_1$ represents the group:

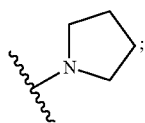

where $Cy_1$ is optionally replaced by one or more $R_4$;

each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring can be oxidized to form groups CO, SO or $SO_2$, and where $Cy_2$ is optionally replaced by one or more $R_4$;

each $R_4$ independently represents $C_{1-4}$alkyl, hydroxyl, $C_{1-4}$alkoxyl, halo$C_{1-4}$-alkyl, hydroxy$C_{1-4}$alkyl or halogen; and n represents 0 or 1.

In another embodiment, the invention refers to the compounds of formula I where:

each $R_1$ independently represents hydrogen, $C_{1-4}$alkoxyl or $Cy_2$;

each $R_3$ independently represents $C_{1-4}$alkyl, halo$C_{1-4}$alkyl or halogen, preferably halo$C_{1-4}$alkyl or halogen;

$R_2$ represents hydrogen;

$Cy_1$ represents the group:

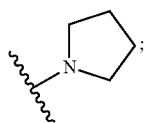

where $Cy_1$ is optionally replaced by one or more $R_4$;

each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring can be oxidized to form groups CO, SO o $SO_2$, and where $Cy_2$ is optionally replaced by one or more $R_4$;

each $R_4$ independently represents $C_{1-4}$alkyl, hydroxyl, $C_{1-4}$alkoxyl, halo$C_{1-4}$alkyl, hydroxy$C_{1-4}$alkyl or halogen; and n represents 0 or 1.

In another embodiment, the invention refers to the compounds of formula I where m represents from 0 to 2, preferably from 0 to 1.

In another embodiment, the invention refers to the compounds of formula I m represents 1.

In another embodiment, the invention refers to the compounds of formula I where n represents 0 or 1.

In another embodiment, the invention refers to the compounds of formula I where:

each $R_1$ and $R_3$ independently represent hydrogen, $C_{1-4}$alkyl, halo$C_{1-4}$alkyl, $C_{1-4}$alkoxyl, halogen or $Cy_2$;

$R_2$ represents hydrogen;

each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring can be oxidized to form groups CO, SO or $SO_2$, and where $Cy_2$ is optionally replaced by one or more $R_4$;

each $R_4$ independently represents $C_{1-4}$alkyl, hydroxyl, $C_{1-4}$alkoxyl, halo$C_{1-4}$alkyl, hydroxy$C_{1-4}$alkyl or halogen;

n represents 0 or 1; and m represents 1.

In another embodiment, the invention refers to the compounds of formula I where:

each $R_1$ independently represents hydrogen, $C_{1-4}$alkoxyl or $Cy_2$;

$R_2$ represents hydrogen;

each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring can be oxidized to form groups CO, SO or $SO_2$, and where $Cy_2$ is optionally replaced by one or more $R_4$;

each $R_4$ independently represents $C_{1-4}$alkyl, hydroxyl, $C_{1-4}$alkoxyl, halo$C_{1-4}$alkyl, hydroxy$C_{1-4}$alkyl or halogen;

n represents 0 or 1; and m represents 1.

In another embodiment, the invention refers to the compounds of formula I where:

each $R_3$ independently represents $C_{1-4}$alkyl, halo$C_{1-4}$alkyl or halogen, preferably halo$C_{1-4}$alkyl or halogen;

$R_2$ represent hydrogen;

each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring can be oxidized to form groups CO, SO or $SO_2$, and where $Cy_2$ is optionally replaced by one or more $R_4$;

each $R_4$ independently represents $C_{1-4}$alkyl, hydroxyl, $C_{1-4}$alkoxyl, halo$C_{1-4}$alkyl, hydroxy$C_{1-4}$alkyl or halogen;

n represents 0 or 1; and m represents 1.

In another embodiment, the invention refers to the compounds of formula I where:

each $R_1$ independently represents hydrogen, $C_{1-4}$alkoxyl or $Cy_2$;

each $R_3$ independently represents $C_{1-4}$alkyl, halo$C_{1-4}$alkyl or halogen, preferably halo$C_{1-4}$alkyl or halogen;

$R_2$ represents hydrogen;

each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring can be oxidized to form groups CO, SO or $SO_2$, and where $Cy_2$ is optionally replaced by one or more $R_4$;

each $R_4$ independently represents $C_{1-4}$alkyl, hydroxyl, $C_{1-4}$alkoxyl, halo$C_{1-4}$alkyl, hydroxy$C_{1-4}$alkyl or halogen;

n represents 0 or 1; and m represents 1.

In another embodiment, the invention refers to the compounds of formula I where:

each $R_1$ independently represents hydrogen, $C_{1-4}$alkoxyl or $Cy_2$;

$R_2$ represents hydrogen;

$Cy_1$ represents a monocyclic heterocycle of 5 or 6 members, saturated or partially unsaturated which is joined to the rest of the molecule by any available N atom, where $Cy_1$ can contain 1 or 2 heteroatoms selected from N, O and S, where one or more atoms of C or S of the ring can be oxidized to form groups CO, SO or $SO_2$, and where $Cy_1$ is optionally replaced by one or more $R_4$;

each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO or $SO_2$, and where $Cy_2$ is optionally replaced by one or more $R_4$;

each $R_4$ independently represents $C_{1-4}$alkyl, hydroxyl, $C_{1-4}$alkoxyl, halo$C_{1-4}$alkyl, hydroxy$C_{1-4}$alkyl or halogen;

n represents 0 or 1; and m represents 1.

In another embodiment, the invention refers to the compounds of formula I where:

each $R_3$ independently represents $C_{1-4}$alkyl, halo$C_{1-4}$alkyl or halogen, preferably halo$C_{1-4}$alkyl or halogen;

$R_2$ represents hydrogen;

$Cy_1$ represents a monocyclic heterocycle of 5 or 6 members, saturated or partially unsaturated which is joined to the rest of the molecule by any available N atom, where $Cy_1$ can contain 1 or 2 heteroatoms selected from N, O and S, where one or more atoms of C or S of the ring may be oxidized to form groups CO, SO or $SO_2$, and where $Cy_1$ is optionally replaced by one or more $R_4$;

each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO or $SO_2$, and where $Cy_2$ is optionally replaced by one or more $R_4$;

each $R_4$ independently represents $C_{1-4}$alkyl, hydroxyl, $C_{1-4}$alkoxyl, halo$C_{1-4}$alkyl, hydroxy$C_{1-4}$alkyl or halogen;

n represents 0 or 1; and m represents 1.

In another embodiment, the invention refers to the compounds of formula I where:

each $R_1$ independently represents hydrogen, $C_{1-4}$alkoxyl or $Cy_2$;

each $R_3$ independently represents $C_{1-4}$alkyl, halo$C_{1-4}$alkyl or halogen, preferably halo$C_{1-4}$alkyl or halogen;

$R_2$ represents hydrogen;

$Cy_1$ represents a monocyclic heterocycle of 5 or 6 members, saturated or partially unsaturated which is joined to the rest of the molecule by any available N atom, where $Cy_1$ can contain 1 or 2 heteroatoms selected from N, O and S, where one or more atoms of C or S of the ring may be oxidized to form groups CO, SO or $SO_2$, and where $Cy_1$ is optionally replaced by one or more $R_4$; each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO or $SO_2$, and where $Cy_2$ is optionally replaced by one or more $R_4$;

each $R_4$ independently represents $C_{1-4}$alkyl, hydroxyl, $C_{1-4}$alkoxyl, halo$C_{1-4}$alkyl, hydroxy$C_{1-4}$alkyl or halogen;

n represents 0 or 1; and m represents 1.

In another embodiment, the invention refers to the compounds of formula I where:

each $R_1$ independently represents hydrogen, $C_{1-4}$alkoxyl or $Cy_2$;

$R_2$ represents hydrogen;

$Cy_1$ represents the group:

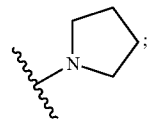

where $Cy_1$ is optionally replaced by one or more $R_4$ each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO or $SO_2$, and where $Cy_2$ is optionally replaced by one or more $R_4$;

each $R_4$ independently represents $C_{1-4}$alkyl, hydroxyl, $C_{1-4}$alkoxyl, halo$C_{1-4}$alkyl, hydroxy$C_{1-4}$alkyl or halogen;

n represents 0 or 1; and m represents 1.

In another embodiment, the invention refers to the compounds of formula I where:

each $R_3$ independently represents $C_{1-4}$alkyl, halo$C_{1-4}$alkyl or halogen, preferably halo$C_{1-4}$alkyl or halogen;

$R_2$ represents hydrogen;

$Cy_1$ represents the group:

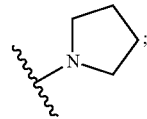

where $Cy_1$ is optionally replaced by one or more $R_4$ each $Cy_2$ independently represents phenyl or an aromatic ring of 5 or 6 members which can be attached to the rest of the molecule by any available C or N atom, where $Cy_2$ contains 1 or 2 heteroatoms selected from N, O and S, where one or more atoms of C or S of the ring may be oxidized to form groups CO, SO or $SO_2$, and where $Cy_2$ is optionally replaced by one or more $R_4$;

each $R_4$ independently represents $C_{1-4}$alkyl, hydroxyl, $C_{1-4}$alkoxyl, halo$C_{1-4}$alkyl, hydroxy$C_{1-4}$alkyl or halogen;

n represents 0 or 1; and m represents 1.

In another embodiment, the invention refers to the compounds of formula I where:

each $R_1$ independently represents hydrogen, $C_{1-4}$alkoxyl or $Cy_2$;

each $R_3$ independently represents $C_{1-4}$alkyl, halo$C_{1-4}$alkyl or halogen, preferably halo$C_{1-4}$alkyl or halogen;

$R_2$ represents hydrogen;

$Cy_1$ represents the group:

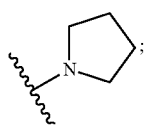

where Cy₁ is optionally replaced by one or more $R_4$;

each Cy₂ independently represents phenyl or an aromatic ring of 5 or 6 members which can be attached to the rest of the molecule by any available C or N atom, where Cy₂ contains 1 or 2 heteroatoms selected from N, O and S, where one or more atoms of C or S of the ring can be oxidized to form groups CO, SO or $SO_2$, and where Cy₂ is optionally replaced by one or more $R_4$;

each $R_4$ independently represents $C_{1-4}$alkyl, hydroxyl, $C_{1-4}$alkoxyl, halo$C_{1-4}$alkyl, hydroxy$C_{1-4}$alkyl or halogen;

n represents 0 or 1; and m represents 1.

Also, the present invention covers all possible combinations of particular and favourite embodiments described above.

In another embodiment, the invention relates to the compounds of formula I that produce more than 50% inhibition of the TCR-Nck interaction in T lymphocytes at 10 μM, more preferably at 1 μM and even more preferably at 0.1 μM, in a TCR-Nck assay in vitro, as described in example 1.

In another embodiment, the invention refers to a compound of formula I selected from among:

ECRA4
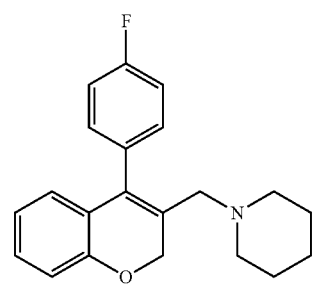

ECRA5
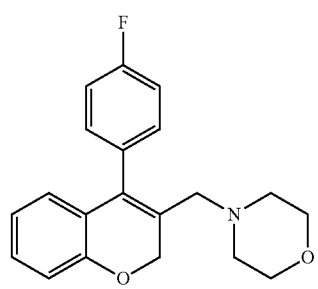

ECRA12
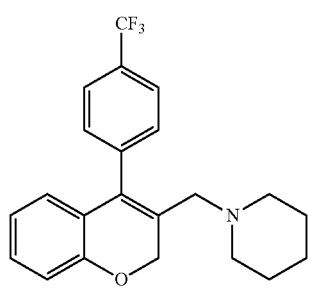

ECRA15
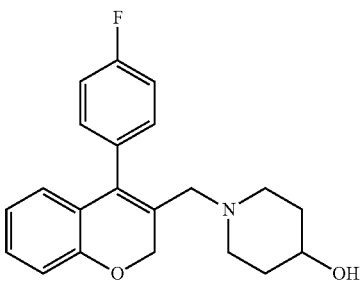

ECRA20
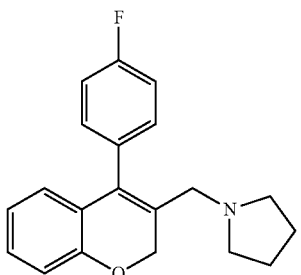

ECRA21
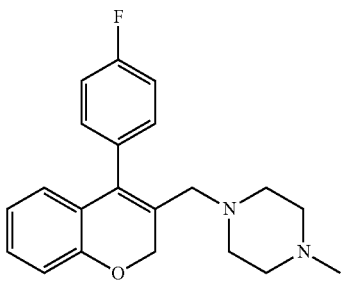

ECRA24
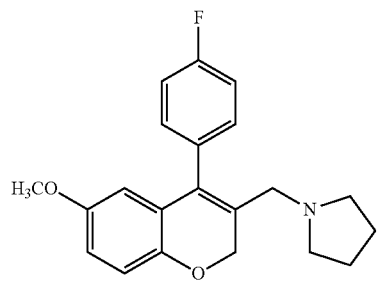

ECRB4
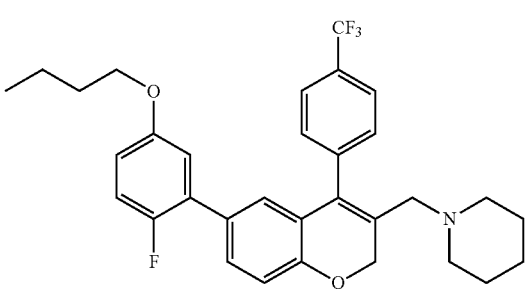

-continued

ECRB5

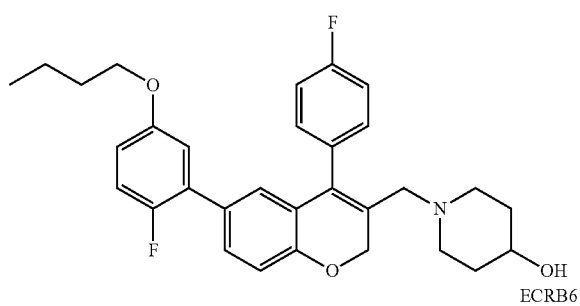

ECRB6

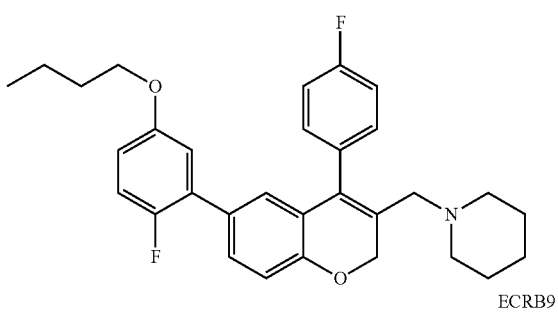

ECRB9

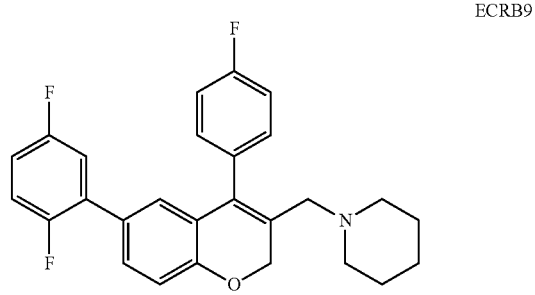

ECRB10

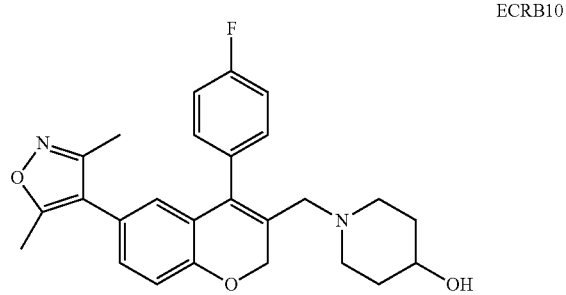 [SMILES: Cc1noc(C)c1-c1ccc2c(c1)C(c1ccc(F)cc1)=C(CN1CCC(O)CC1)CO2]

The compounds of the present invention contains one or more basic nitrogen and, therefore, could form salts with both organics and inorganic acids. Examples of these salts include: salts with inorganic acids such as hydrochloric acids, hydrobromic acid, hydroiodic acid, nitric acid, perchloric acid, sulfuric acid or phosphoric acid, and salts with organic acids such as methanesulfonic acid, trifluoromethanesulfonic acid, ethanesulfonic acid, benzenesulfonic acid, p-toluenesulfonic acid, fumaric acid, oxalic acid, acetic acid, maleic acid, ascorbic acid, citric acid, lactic acid, tartaric acid, malonic acid, glycolic acid, succinic acid and propionic acid, among others. Some compounds of the present invention could contain one or more acidic protons and therefore could also form salts with bases. Examples of these salts include: salts with inorganic cations such as sodium, potassium, calcium, magnesium, lithium, aluminium, zinc, etc.; and salts formed with pharmaceutically acceptable amines such as ammonia, alkylamines, hydroxyalkylamines, lysine, arginine, N-methylglucamine, procaine and similar.

There is no limitation on the type of salt that can be used, with the condition that when used for therapeutic purpose they should be pharmaceutically acceptable. Pharmaceutically acceptable salts means those salts which, according to a medical criteria, are suitable for use in contact with the human tissues or other mammals without causing undue toxicity, irritation, allergic response or similar. The pharmaceutically acceptable salts are widely known to a person skilled in the art.

Salts of a compound of formula I can be obtained during the final isolation and purification of the compounds of the invention or can be prepared by treatment of a compound of formula I with the sufficient amount of the desired acid or base to give a salt in a conventional way. Salts of the compound of formula I can be transformed in turn into other salts of compounds of formula I by ion exchange using an ionic exchange resin.

The compounds of formula I and their salts may differ in some physical properties, but they are equivalent for purposes of the invention. All salts of the compounds of formula I are included within the scope of the invention.

The compounds of the present invention can form complexes with solvents where they are made to react or from those from where they are made to precipitate or crystallize. These complexes are known as solvates. As used herein, the term solvate refers to a complex of variable stoichiometry formed by a solute (a compound of formula I or a salt thereof) and a solvent. Examples of solvents include pharmaceutically acceptable solvents such as water, ethanol and similar. A complex with water is known as a hydrate. Solvates of the compounds of the invention (or salts thereof), including hydrates, are included within the scope of the invention.

The compounds of formula I may exist in different physical forms, namely in amorphous and crystalline forms. Likewise, compounds of the present invention may be able to crystallize in more than one form, a characteristic known as polymorphism. Polymorphs can be distinguished by various physical properties well known to those skilled in the art such as X-ray diffractograms, melting points or solubilities. All physical forms of the compounds of formula I, including all polymorphic forms ("polymorphs") are included within the scope of the present invention.

Some compounds of the present invention can exist as several diastereoisomers and/or several optical isomers. The diastereomers can be separated by conventional techniques such as chromatography or fractional crystallization. The optical isomers can be resolved using conventional techniques of optical resolution to give optically pure isomers. This resolution can be carried out on synthesis intermediates that are chiral or upon the products of formula I. The optically pure isomers can also be individually obtained using enantiospecific synthesis. The present invention covers both the individual isomers and their mixtures (for example racemic mixtures or mixtures of diastereomers), whether obtained by synthesis or physically mixed.

The compounds of formula I can be obtained by following the procedures described below. As it will be obvious to a person skilled in the art, the precise method used for the preparation of a given compound may vary according to its chemical structure. In some of the procedures listed below may be necessary or desirable to protect reactive or labile groups by conventional protective groups. Both the nature of such protective groups and the procedures for its introduction and removal are well known and are part of the state of the art (see for example T. W. Greene and Wuts P. G. M, "Protective Groups in Organic Synthesis", John Wiley & Sons 3rd edition, 1999). For example, as a protective group of an amino function can be used a tetrahydropyranyl group (THP). Whenever any protective group is present, a final deprotection stage will be necessary, which is done under standard conditions in organic synthesis, as described in the reference mentioned above.

Except otherwise indicated, in the methods that are described below the meanings of the various substituents are the meanings described above in relation to a compound of formula I.

In general, the compounds of formula I can be obtained by the method described in diagram 1:

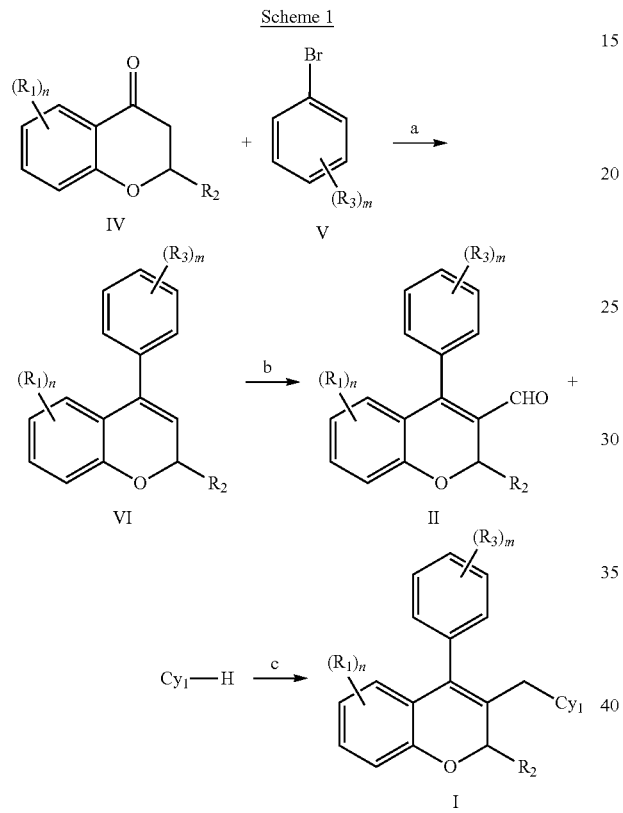

where $R_1$, $R_2$, $R_3$, $Cy_1$, n and m have the meaning described above in relation to a compound of formula I.

On stage a, the reaction between a compound of formula IV and the bromoderivative of formula V in the presence of a metal such as magnesium (Grignard conditions), in the presence of a solvent such as tetrahydrofuran gives rise to a compound of formula VI.

Stage b of formylation can be carried out between a compound of formula VI with phosphoryl chloride and dimethylformamide to obtain a compound of formula II.

Stage c can be performed between a compound of formula II with a compound of formula III to get in one or more stages of reaction, a compound of formula I. An example of this type of reaction is the reductive amination of a compound of formula II in the presence of a compound of formula III to obtain a compound of formula I.

The compounds of formula III, IV and V are commercially available or can be prepared by methods widely described in the literature, and may be suitably protected.

Also, some compounds of the present invention can be obtained from other compounds of formula I through the right transformational reactions of functional groups, in one or more stages, using reactions widely known in organic chemistry under the usual experimental conditions.

Such conversions include, for example:
the reduction of a nitro group to an amino group, for example by treatment with hydrogen, hydrazine or formic acid in the presence of a suitable catalyst as Pd/C; or by treatment with sodium borohydride in the presence of $NiCl_2$, or the $SnCl_2$;

the replacement of a primary or secondary amine by treatment with an alkylating agent under standard conditions; or by reductive amination, i.e., by treatment with an aldehyde or ketone in the presence of a reducing agent such as sodium cyanoborohydride or sodium triacetoxyborohydride;

the transformation of an amine in a sulfonamide by reaction with a sulfonyl halide such as sulfonyl chloride, optionally in the presence of catalytic amounts of a base such as 4-dimethylaminopyridine, in a suitable solvent such as diethyl ether, chloroform, dichloromethane or pyridine, optionally in the presence of a base such as triethylamine or pyridine;

the transformation of an amine in an amide, carbamate or urea under standard conditions;

the alkylation of an amide by treatment with an alkylating agent under basic conditions;

the conversion of an alcohol in an ether, ester or carbamate under standard conditions;

the alkylation of a thiol to obtain thioether, in standard conditions the total or partial oxidation of an alcohol to ketone, aldehyde, or carboxylic acids in standard conditions of oxidation;

the reduction of an aldehyde or ketone to alcohol, by treatment with a reducing agent such as sodium borohydride;

the reduction of a carboxylic acid or a derivative of a carboxylic acid to alcohol by treatment with a reducing agent such as diisobutylaluminium hydride or $LiAlH_4$;

the oxidation of a thioether to sulfoxide or sulfone in standard conditions;

the transformation of an alcohol into a halogen by treatment with $SOCl_2$, $PBr_3$, tetrabutylammonium bromide in the presence of $P_2O_5$, or $PI_3$;

the transformation of an halogen atom in an amine by reaction with an amine, optionally in the presence of a suitable solvent, and preferably by heating;

the transformation of a primary amide in a group —CN or vice versa, of a group —CN in a amide trough standard conditions.

Also, any of the aromatic rings of the compounds of the present invention may experience a reaction of electrophilic aromatic substitution or nucleophilic aromatic substitution, widely described in the literature.

Some of these conversion reactions are explained in more detail in the examples.

As it will be apparent to those skilled in the art, these conversion reactions can be performed both on the compounds of formula I or on any suitable synthesis intermediate.

As previously mentioned, the compounds of this invention act by inhibiting TCR-Nck interaction in T lymphocytes. Therefore, these compounds might be useful for the treatment of those diseases in which the participation of the TCR-Nck interaction in T lymphocytes is important in mammals, including humans. Such diseases include, without limitation, transplants rejection; immune, autoimmune or inflammatory diseases; neurodegenerative diseases; and proliferative disorders (see for example O'Shea J. J. et al, Nat. Rev. Drug Discov. 2004, 3(7):555-64; Cetkovic-Cvrlje M. et al, Curr.

Pharm. Des. 2004, 10(15):1767-84; Cetkovic-Cvrlje M. et al, Arch. Immunol. Ther. Exp. (Warsz), 2004, 52(2):69-82).

For example, among the reactions of rejection of transplants, both acute and chronic, which can be treated with compounds of the present invention are included any type of xenotransplantation or cell allografts, tissues or organs, such as heart, lung, liver, kidney, pancreas, uterus, joints, pancreatic islet, bone marrow, member, cornea, skin, hepatocytes, pancreatic beta cells, stem cells, neuronal cells and myocardial cells, as well as graft versus host reactions (see for example Rousvoal G. et al, Transpl Int 2006, 19(12):1014-21; Borie D C. et al, Transplantation 2005, 79(7):791-801; Paniagua R. et al, Transplantation 2005, 80(9):1283-92; Higuchi T. et al, J Heart Lung Transplant. 2005, 24(10):1557-64; Säemann M D. et al, Transpl. Int. 2004, 17(9):481-89; Silva Jr H T. et al, Drugs 2006, 66(13):1665-1684).

Among the immune, autoimmune or inflammatory diseases that can be treated with the compounds of the invention include rheumatic diseases (e.g. rheumatoid arthritis and psoriatic arthritis), autoimmune hematological disorders (e.g. hemolytic anemia, aplastic anemia idiopathic thrombocytopenia and neutropenia), autoimmune gastritis and intestinal inflammatory diseases (e.g. ulcerative colitis and Crohn's disease), scleroderma, type I diabetes and complications of diabetes, hepatitis B, hepatitis C, primary biliary cirrhosis, myasthenia gravis, multiple sclerosis, lupus erythematosus, psoriasis, atopic dermatitis, contact dermatitis, eczema, sunburn of skin, HIV replication suppression, infertility of autoimmune origin, thyroid disease of autoimmune origin (Grave's disease), interstitial cystitis and allergic reactions mediated by mast cells such as asthma, bronchitis, anaphylaxis, angioedema, rhinitis and sinusitis (see for example Sorbera L A. et al, Drugs of the Future 2007, 32(8):674-680; O'Shea J. J. et al, Nat. Rev. Drug. Discov. 2004, 3(7):555-64; Cetkovic-Cvrlje M. et al, Curr. Pharm. Des. 2004, 10(15): 1767-84; Muller-Ladner U. et al, J. Immunol. 2000, 164(7): 3894-3901; Walker J G. et al, Ann. Rheum. Dis. 2006, 65(2): 149-56; Milici A J. et al, Arthritis Rheum. 2006, 54 (9, Suppl): abstr 789; Kremer J M. et al, Arthritis Rheum. 2006, 54, 4116, presentation no. L40; Cetkovic-Cvrlje M. et al, Arch. Immunol. Ther. Exp. (Warsz), 2004, 52(2):69-82; Malaviya R. et al, J. Pharmacol. Exp. Ther. 2000, 295(3):912-26; Malaviya R. et al, J. Biol. Chem. 1999, 274(38):27028-38; Wilkinson B et al, Ann. Rheum. Dis. 2007, 66(Suppl 2): Abst THU0099; Matsumoto M. et al, J Immunol. 1999, 162(2):1056-63).

As example of neurodegenerative diseases that can be treated with the compounds of the invention it can be included the amyotrophic lateral sclerosis and Alzheimer's disease (see for example Trieu V N. et al, Biochem. Biophys. Res. Commun. 2000, 267(1):22-5).

As examples of proliferative disorders that can be treated with the compounds of the invention it can be included lymphomas, leukemias, colon carcinoma, glioblastoma multiforme, as well as thromboembolic and allergic complications associated with these diseases (see for example Sudbeck E A. et al, Clin. Cancer Res. 1999, 5(6):1569-82; Narla R K. et al, Clin. Cancer Res. 1998, 4(10):2463-71; Lin Q. et al, Am J. Pathol. 2005, 167(4):969-80; Tibbles H E. et al, J. Biol. Chem. 2001, 276(21):17815-22).

The biological tests that can be used to determine the ability of a compound to inhibit TCR-Nck interaction in T lymphocytes are widely known. For example, a compound that inhibits the TCR-Nck interaction such as shown in example 1, must inhibit the polymerization of the actin cytoskeleton induced in T lymphocytes after TCR stimulation, as shown in example 2. Other in vitro assays that can be used to measure the inhibitory activity of the interaction of TCR-Nck in T lymphocytes include cellular assays, as for example, inhibition of proliferation of T lymphocytes after stimulation of the TCR (example 3) and inhibition of secretion of cytokines by T lymphocytes caused by stimulation of the TCR (example 4). The immunosuppressive activity of the compounds of the present invention can be assayed using standard in vivo animal models for immune and autoimmune diseases, which are well known and are part of the state of the art. For example, you can use the following tests: delayed hypersensitivity, (delayed-type hypersensitivity, DTH) (see for example the method described at Kudlacz e. et al, Am. J. Transplant. 2004, 4 (1): 51-7, whose content is incorporated here by reference), models of rheumatoid arthritis such as collagen-induced arthritis (see for example the method described in Holmdahl R et al, APMIS, 1989, 97 (7): 575-84, whose content is incorporated here by reference), models of multiple sclerosis, such as experimental autoimmune encephalomyelitis (experimental autoimmune encephalomyelitis, EAE) (see for example the method described in Gonzalez-rey et al, Am. J. Pathol. 2006, 168 (4): 1179-88, whose content is incorporated here by reference) and models of transplant rejection (see for example various animal models described in the references above in relation to the treatment of transplant rejection, incorporated here by reference).

In order to select active compounds, 10 µM trials should result in an activity of more than 50% of inhibition in the test mentioned in Example 1. More preferably, compounds should present more than 50% inhibition at 1 µM, and even more preferably, should present more than 50% inhibition at 0.1 µM.

The present invention also refers to a pharmaceutical composition comprising a compound of the invention (or a salt or pharmaceutically acceptable solvate thereof) and one or more pharmaceutically acceptable excipient. Excipients must be "acceptable" in the sense of being compatible with the other ingredients of the composition and not be harmful to those taking such composition.

The compounds of this invention can be administered in the form of any pharmaceutical formulation, the nature of which, as it is well known, will depend on the nature of the active principle and its route of administration. In principle any route of administration can be used, e.g. oral, parenteral, nasal, eye, rectal, and topical.

Solid compositions for oral administration include granules, tablets and capsules. In any case the manufacturing method is based on a simple mixture, dry or wet granulation of the active substance with excipients. These excipients may be, for example, thinners such as lactose, microcrystalline cellulose, mannitol, or hydrogenphosphate calcium; binding agents such as starch, gelatin or polyvinylpyrrolidone; disintegrants such as sodium carboxymethyl starch or sodium croscarmellose; and lubricants agents such as magnesium stearate, stearic acid or talc. The tablets can also be coated with suitable excipients and by known techniques with the object of delaying its disintegration and absorption in the gastrointestinal tract and thus get a sustained action over a longer period of time, or simply to improve its organoleptic properties or its stability. The active ingredient can also be incorporated by coating on inert pellets through the use of natural or synthetic film-forming polymers. It is also possible the generation of soft gelatin capsules, in which the active ingredient is mixed with water or oily medium, for example coconut oil, liquid paraffin, or olive oil.

It is possible to get powders and granulates for the preparation of oral suspensions by the addition of water, mixing the active principle with dispersing and wetting agents; suspending agents and preservatives. They can also add other excipients, such sweeteners, flavourings and colourings.

As for liquid forms for oral administration it can be included emulsions, solutions, suspensions, syrups and elixirs containing inert solvents commonly used, such as distilled water, ethanol, sorbitol, glycerol, polyethylene glycols (macrogols) and propylene glycol. These compositions can also contain adjuvants such as wetting agents, suspending agents, sweeteners, flavourings, preservatives and pH regulators.

Injectable preparations, in accordance with the present invention, for parenteral administration, include solutions, suspensions or sterile emulsions, in aqueous or not aqueous solvents such as propylene glycol, polyethylene glycol or vegetable oils. These compositions may also contain co-adjuvants, as moisturizers, emulsifiers, dispersing agents, and preservatives. They could be sterilized by any of the known methods or prepared as solid sterile compositions, which will be dissolved in water or any other injectable sterile vehicle immediately before use. It is also possible to start from sterile raw materials and keep them in these conditions throughout the manufacturing process.

For rectal administration, the active substance can be formulated preferably as a suppository in an oil-based, such as vegetable oils or semi-synthetic solid glycerides, or in a hydrophilic base as polyethylene glycols (macrogol).

The compounds of the invention can also be formulated for topical application for the treatment of pathologies in areas or organs accessible trough this route, such as eye, skin and intestinal tract. Formulations include creams, lotions, gels, powders, solutions and patches in which the compound is dispersed or dissolved in suitable excipients.

For nasal administration or inhalation, compound may be formulated in the form of spray where it is conveniently released with the employment of suitable propellants.

The dosage and frequency of the dose will vary depending on the nature and severity of the disease to be treated, age, general condition and the patient's weight, as well as also the particular compound administered and the route of administration, among other factors. For example, a suitable dosage range varies between around 0.01 mg/Kg and about 100 mg/Kg per day, which can be administered as a single dose or in several intakes.

The invention is then illustrated by the following examples.

EXAMPLES

Figure 1:
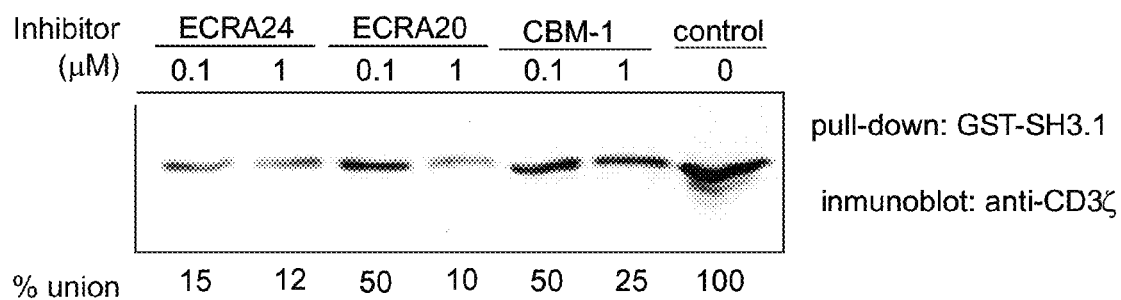
FIG. 1: Shows the inhibitory effect of the compounds ECRA20, ECRA24, and CBM-1 (described in WO2010000900, which is incorporated here by reference) on the interaction between TCR, through CD3ϵ, and the Nck SH3.1 domain in an in vitro "pull-down" assay.

The synthesis of the compounds described was addressed using commercially available reagents without prior purification and conventional quality solvents, except when anhydrous conditions were necessary, where solvents coming from an anhidrization system "Pure Solv™ Solvent Purification System" were used Purification by column chromatography was carried out using silica 60 A C.C. 35-70 µm and in the preparative chromatography, it was used plates of silica gel 60 to F254 0.5 nm.

The purity and identity of the described compounds were determined by nuclear magnetic resonance (NMR) and mass spectrometry. The NMR experiments were performed in deuterated chloroform and at room temperature, using a Varian Unity 400 device (400 MHz). The accurate mass determination was carried out with an Acquity UPLC Waters unit using the electroespray ionization technique for the detection and acetonitrile-water mixtures as eluent.

Examples ECRA24

1-((4-(4-Fluorophenyl)-6-methoxy-2H-chromen-3-yl)methyl)pyrrolidine a) 4-(4-Fluorophenyl)-6-methoxy-2H-chromene

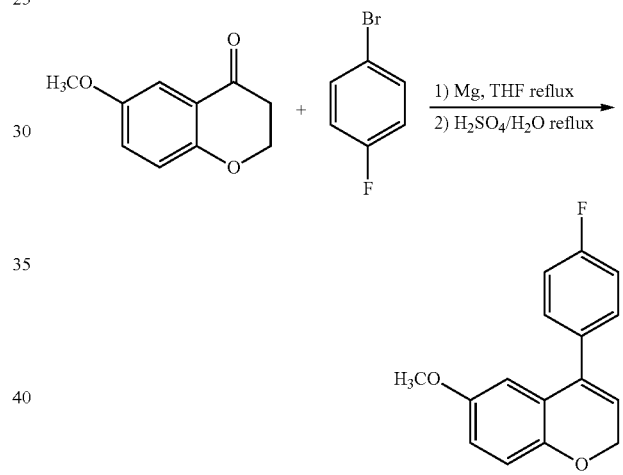

A dissolution of 4-fluor-1-bromobencen (1.5 eq) in anhydrous THF (8 ml/nmol of bromo derivative), was added drop by drop under inert atmosphere over magnesium turnings (10 eq.). The mixture was activated by the addition of 1,2-dibromoethane and heated to reflux for 3 h. Once cooled to room temperature, a solution of the corresponding 6-metoxicroman-4-on a (1 eq.) was added dropwise in anhydrous THF (12 ml/mmol chromanone) and the mixture was heated to reflux for 3.5 h (Glennon, R. A.; Liebowitz, S. J. Med. Chem. 1982, 24 (4), 393-397). Once cooled at room temperature, saturated aqueous NH$_4$Cl (12 ml/mmol chromanone) was added over 15 minutes. The product was extracted with t-butyl methyl ether (3×5 ml/mmol chromanone) and the combined organic phases were washed with saturated aqueous NaHCO$_3$ until neutral, dried (MgSO$_4$) and solvent was evaporated under reduced pressure.

Then, the crude from the previous step was dissolved in dioxane (2 ml/mmol chromanone), an aqueous solution of H$_2$SO$_4$ 20% v/v (12 ml/mmol chromanone) was added and heated at reflux for 3 h. The mixture was allowed to cool down to room temperature and neutralized. After evaporation of the dioxane, the product was extracted with t-butyl methyl ether (3×5 ml/mmol chromanone), washed with water, dried (MgSO$_4$) and solvent evaporated under reduced pressure giving rise to the corresponding 4-(4-Fluorophenyl)-6-methoxy-2H-chromene as a white solid. If necessary, the product can be purified by column chromatography (silica, hexane/ethyl acetate 20:1).

b) 4-(4-Fluorophenyl)-3-formyl-6-methoxy-2H-chromene

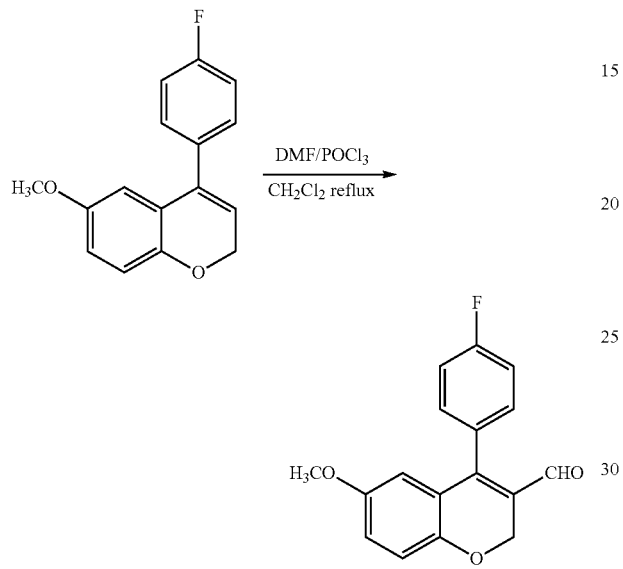

To a solution of anhydrous DMF (2 eq.) and POCl$_3$ (2 eq.) in CH$_2$Cl$_2$ (3 ml/mmol substrate), at room temperature and under inert atmosphere, the substrate was added from the previous step (1 eq.) and the mixture was heated by reflux (18 h). Once the reaction was completed it was poured onto ice/water. Then, it was extracted with t-butylmethyl ether, washed successively with 1N HCl, saturated NaHCO$_3$ and water, and dried with MgSO$_4$. Evaporation of the solvent under reduced pressure led to the product 4-(4-fluorophenyl)-3-formyl-6-methoxy-2H-chromene, which was used in the next step without further purification.

c) 1((4-(4-Fluorophenyl)-6-methoxy-2H-chromen-3-yl)methyl)pyrrolidine (ECRA24)

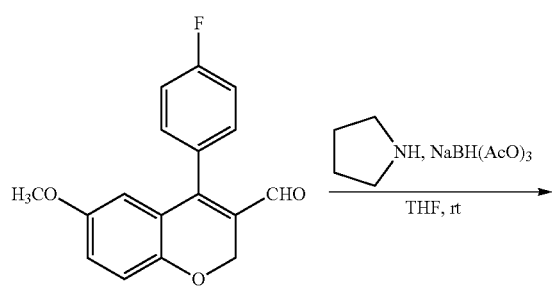

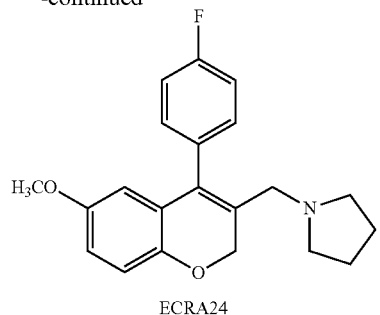

ECRA24

To a solution of the substrate obtained in the above step (1 eq.) and pyrrolidine (1.1 eq.) in THF (4 ml/mmol substrate) at room temperature and inert atmosphere, it was added NaBH(OAc)$_3$ (1.5 eq.) and the mixture was stirred overnight. Once the reaction was concluded a saturated NaHCO$_3$ was added, extracted with t-BuMeO, dried (MgSO$_4$) and evaporated under reduced pressure. Purification by preparative chromatography (silica, hexane/ethyl acetate 4:1) led to the title product as a white solid (60-90%).

$^1$HRMN (CDCl$_3$, 400 MHz): 7.13-7.10 (m, 4H), 6.81 (d, 1H), 6.66 (dd, 1H), 6.14 (d, 1H), 4.86 (s, 2H), 3.62 (s, 3H), 3.04 (s, 2H), 2.38 (m, 4H), 1.72-1.69 (m, 4H). HRMS (electroespray): teor. C$_{21}$H$_{22}$FNO$_2$+1: 340.1713; exp.: 340.1699.

Following an analogous procedure to obtaining ECRA24 compound, the following compounds were obtained:

Example ECRA4

1-((4-(4-Fluorophenyl)-2H-cromen-3-il)methyl)piperidine $^1$HRMN (CDCl$_3$, 400 MHz): 7.13-7.11 (m, 5H), 6.87 (d, 1H), 6.77 (t, 1H), 6.55 (d, 1H), 4.89 (s, 2H), 2.94 (s, 2H), 2.31-2.29 (m, 4H), 1.55-1.53 (m, 4H), 1.38-1.37 (m, 2H). HRMS (electroespray): teor. C$_{21}$H$_{22}$FNO+H: 324.1764; exp.: 324.1762.

Example ECRA5

4-((4-(4-Fluorophenyl)-2H-cromen-3-il)methyl)morpholine $^1$HRMN (CDCl$_3$, 400 MHz): 7.14-7.11 (m, 5H), 6.88 (d, 1H), 6.81 (t, 1H), 6.57 (d, 1H), 4.90 (s, 2H), 3.67 (s, 4H), 2.94 (s, 2H), 2.34 (m, 4H). HRMS (electroespray): teor. C$_{20}$H$_{20}$FNO$_2$+H; 326.1556; exp.: 326.1562.

Example ECRA12

1-((4-(4-(Trifluoromethyl)phenyl]-2H-cromen-3-il)methyl)piperidine $^1$HRMN (CDCl$_3$, 400 MHz): 7.68 (d, 2H), 7.29 (d, 2H), 7.09 (t, 1H), 6.87 (d, 1H), 6.75 (t, 1H), 6.49 (d, 1H), 4.90 (s, 2H), 2.86 (s, 2H), 2.25 (m, 4H), 1.52-1.50 (m, 4H), 1.37-1.36 (m, 2H). HRMS (electroespray): teor. C$_{22}$H$_{21}$F$_3$NO+H: 374.1732; exp.: 374.1707.

Example ECRA15

1-((4-(4-Fluorophenyl)-2H-cromen-3-il)methyl)piperidin-4-ol $^1$HRMN (CDCl$_3$, 400 MHz): 7.11-7.10 (m, 5H), 6.86 (d, 1H), 6.76 (t, 1H), 6.55 (dd, 1H), 4.88 (s, 2H), 3.62 (m, 1H), 2.94 (s, 2H), 2.90 (s, 2H), 2.65-2.64 (m, 2H), 1.84-1.80 (m, 2H), 1.56-1.47 (m, 2H), 1.27-1.24 (m, 2H). HRMS (electroespray): teor. $C_{21}H_{22}FNO_2$+H: 340.1713; exp.: 340.1699.

Example ECRA20

1-((4-(4-Fluorophenyl)-2H-cromen-3-il)methyl)pyrrolidine $^1$HRMN (CDCl$_3$, 400 MHz): 7.14-7.12 (m, 5H), 6.88 (d, 1H), 6.78 (t, 1H), 6.57 (dd, 1H), 4.93 (s, 2H), 3.05 (s, 2H), 2.41 (m, 4H), 1.73-1.71 (m, 4H). HRMS (electroespray): teor. $C_{20}H_{20}FNO$+H: 310.1607; exp.: 310.1628.

Example ECRA21

1-((4-(4-Fluorophenyl)-2H-cromen-3-il)methyl)-4-methylpiperazine $^1$HRMN (CDCl$_3$, 400 MHz): 7.11-7.09 (m, 5H), 6.86 (d, 1H), 6.77 (t, 1H), 6.56 (dd, 1H), 4.86 (s, 2H), 2.92 (s, 2H), 2.27 (m, 4H). HRMS (electroespray): teor. $C_{21}H_{23}FN_2O$+H: 339.1873; exp.: 339.1860.

Example ECRB4

1-((6-(5-Butoxy-2-fluorophenyl)-4-(4-(trifluoromethyl)phenyl)-2H-cromen-3-il)methyl)piperidine $^1$HRMN (CDCl$_3$, 400 MHz): 7.69 (d, 2H), 7.34-7.29 (m, 3H), 6.96-6.95 (d, 2H), 6.74-6.72 (m, 3H), 4.95 (s, 2H), 3.89 (t, 2H), 2.90 (s, 2H), 2.26 (m, 4H), 1.72 (q, 2H), 1.54-1.51 (m, 4H), 1.49-1.43 (m, 2H), 1.37 (ma, 2H), 0.96 (t, 3H). HRMS (electroespray): teor. $C_{32}H_{33}F_4NO_2$+H: 540.2526; exp.: 540.2557.

Example ECRB5

1-((6-(5-Butoxy-2-fluorophenyl)-4-(4-fluorophenyl)-2H-cromen-3-il)methyl) piperidin-4-ol $^1$HRMN (CDCl$_3$, 400 MHz): 7.29-7.26 (m, 2H), 7.13-7.10 (m, 4H), 6.93 (d, 2H), 6.73-6.72 (m, 2H), 4.92 (s, 2H), 3.89 (t, 2H), 3.63 (ma, 1H), 2.94 (s, 2H), 2.67-2.65 (m, 4H), 1.72 (q, 2H), 1.70-1.42 (m, 6H), 0.95 (t, 3H). HRMS (electroespray): teor. $C_{31}H_{33}F_2NO_3$+H: 506.2507; exp.: 506.2458.

Example ECRB6

1-((6-(5-Butoxy-2-fluorophenyl)-4-(4-fluorophenyl)-2H-cromen-3-il)methyl) piperidine $^1$HRMN (CDCl$_3$, 400 MHz): 7.27 (d, 1H), 7.17-7.08 (m, 4H), 6.93 (d, 2H), 6.74-6.72 (m, 3H), 4.93 (s, 2H), 3.89 (t, 2H), 2.90 (s, 2H), 2.26 (m, 4H), 1.74 (q, 2H), 1.53-1.51 (m, 4H), 1.47-1.45 (m, 2H), 1.36 (ma, 2H), 0.96 (t, 3H). HRMS (electroespray): teor. $C_{31}H_{33}F_2NO_2$+H: 490.2558; exp.: 490.2559.

Example ECRB9

1-((6-(2,5-Difluorophenyl)-4-(4-fluorophenyll)-2H-cromen-3-il)methyl)piperidine $^1$HRMN (CDCl$_3$, 400 MHz): 7.24-7.11 (m, 6H), 6.93 (d, 2H), 6.83-6.77 (m, 2H), 6.66 (s, 1H), 4.94 (s, 2H), 2.91 (s, 2H), 2.27 (ma, 4H), 1.53 (ma, 4H), 1.36 (sa, 2H. HRMS (electroespray): teor. $C_{27}H_{24}F_3NO$+H: 436.1888; exp.: 436.1902.

Example ECRB10

1-((6-(3,5-Dimethylisoxazol-4-il)-4-(4-fluorophenyl)-2H-cromen-3-il)methyl) piperidin-4-ol $^1$HRMN (CDCl$_3$, 400 MHz): 7.12-7.10 (d, 4H), 6.99 (dd, 1H), 6.92 (d, 1H), 6.38 (d, 1H), 4.95 (s, 2H), 3.66 (ma, 1H), 2.98 (s, 2H), 2.68-2.67 (m, 2H), 2.23 (s, 3H), 2.09 (s, 3H), 2.09 (ma, 2H), 1.86-1.85 (ma, 2H), 1.56-1.54 (ma, 2H). HRMS (electroespray): teor. $C_{26}H_{27}FN_2O_3$+H: 435.2084; exp.: 435.2098.

Example 1

In Vitro Inhibition of the TCR-Nck Interaction

The effect of the compounds ECRA20, ECRA24, and CBM-1 (described in WO2010000900, which is incorporated here by reference) on the TCR-Nck in vitro interaction, was shown in a "pull-down" test in which the interaction between the TCR from T-lymphocytes lysate with purified protein GST-SH3.1 (Nck) immobilized on agarose beads, was revealed by Western blot with anti-CD3 antibody. To do so, 10 million from human T cell line Jurkat were stimulated with 10 µg/ml of an anti-CD3 antibody for 5 minutes at 37° C. After the stimulation, the cells were lysed in isotonic buffer containing 0.3% Brij96 detergent. After removing the nucleus and other cellular debris by centrifugation, cell lysate aliquots were incubated with 10 µl of agarose beads covalently bound to glutathione and bound in turn to 5 µg of purified GST-SH3.1 (Nck) protein from bacterial cultures. The GST-SH3.1 (Nck) protein corresponds to a fusion protein between glutathione S-transferase (GST) and the amino-terminal human Nck1 SH3.1 domain. Each of the aliquots of the cell lysate were incubated with GST-SH3.1 (Nck) in the presence of the indicated concentrations of inhibitors. After incubation, the agarose beads were collected by centrifugation and the quantity of TCR associated with GST-SH3.1 (Nck) was assessed by SDS-PAGE and Western blot with an antibody against TCR CD3ζ subunit. The quantification of the ratio between the quantity of TCR joined to GST-SH3.1 (Nck) in the presence of each of the concentrations of inhibitors, with respect to the amount that is attached in the absence of inhibitors, was evaluated by densitometry and is expressed under each rail as a percentage (FIG. 1).

Example 2

Figure 2:
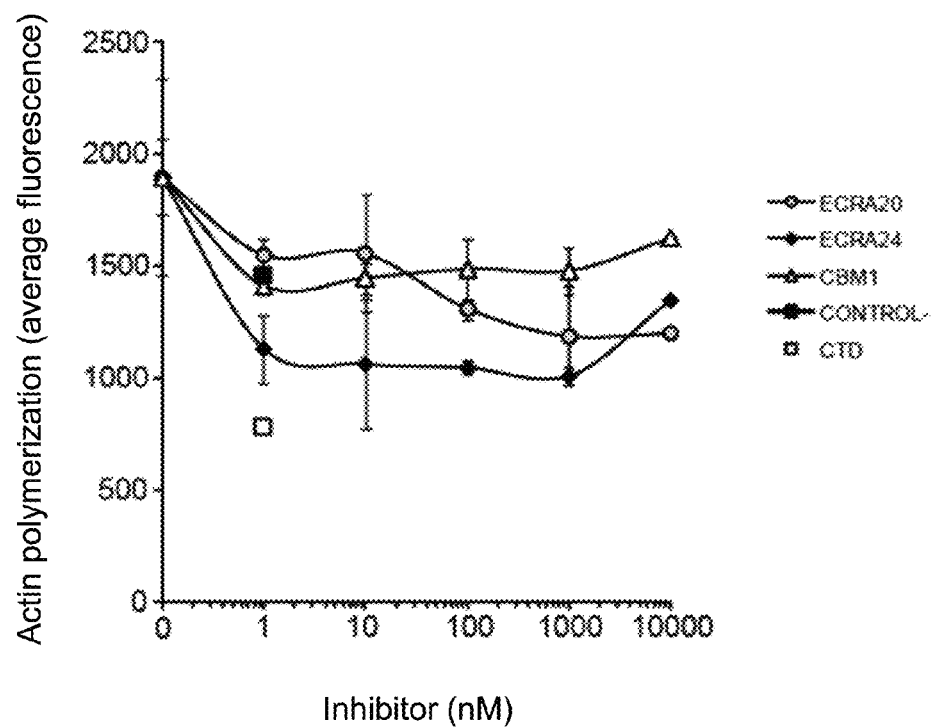
FIG. 2: Shows the effect of the compounds ECRA20, ECRA24, and CBM-1 on the polymerization of the actin cytoskeleton induced in T lymphocytes after stimulation of the TCR. NCK has a well known role in the polymerization of the actin cytoskeleton.

Inhibition of Polymerization of the Actin Cytoskeleton in T Lymphocytes Caused by Stimulation of the TCR The effect of the ECRA20, ECRA24, and CBM-1 compounds on the TCR ability to activate the polymerization of actin cytoskeleton was evaluated in primary T lymphocytes obtained from blood of healthy human donors. T lymphocytes were stimulated for 5 minutes at 37° C. with 10 µg/ml of an anti-CD3 antibody in the presence of the indicated concentrations of compounds, after which the cells were fixed, permeabilized with detergent, and the polymerization of the actin cytoskeleton was measured by staining with Phalloidin-FITC and analysed by flow cytometry. The 0 point In the axis of ordinates of the graph indicates the polymerization of actin produced after the TCR stimulation, while the black square indicates the baseline level of polymerization of actin in cells not stimulated with anti-CD3 (control–). White square is a control of inhibition which uses a known inhibitor of actin polymerization cytochalasin D at 10 μg/ml on lymphocytes stimulated with anti-CD3 (FIG. 2).

Example 3

Figure 3:
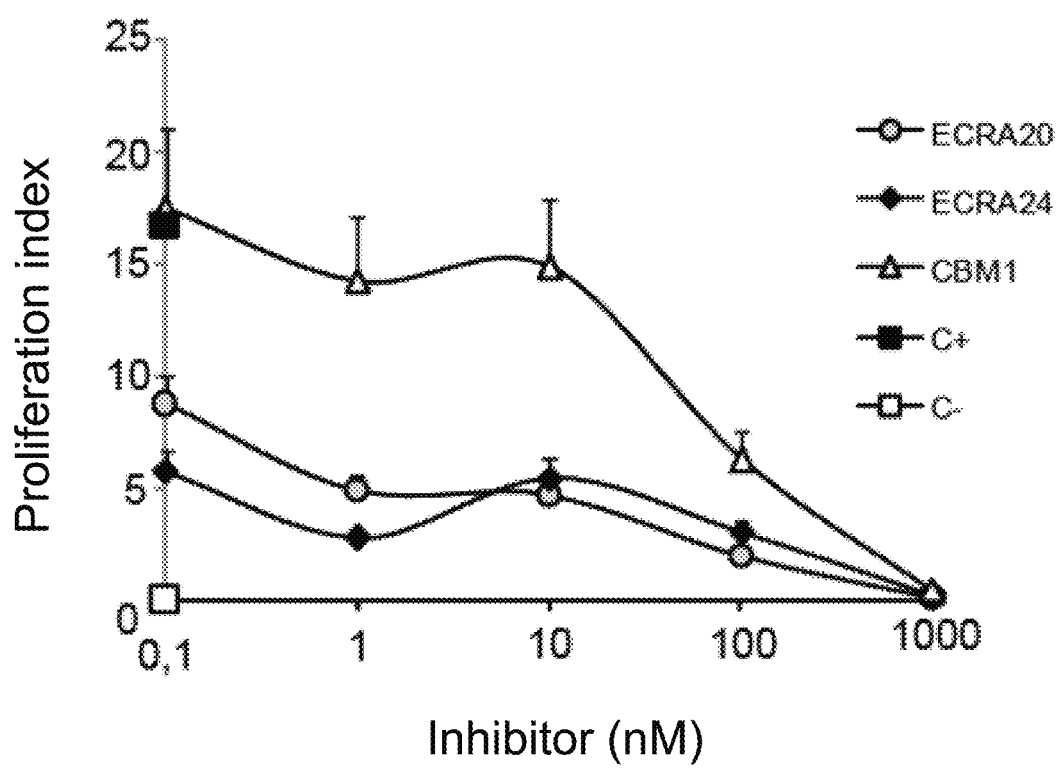
FIG. 3: ECRA20, ECRA24, and CBM-1 compounds suppress the proliferation of T lymphocytes in response to stimulation of the TCR. This shows that the mentioned compounds have a suppressive effect on the activation of T-lymphocytes.

Inhibition of the Proliferation of T Lymphocytes Caused by Stimulation of the TCR The effect of compounds ECRA20, ECRA24 and CBM-1 on the ability of the TCR to induce T lymphocyte proliferation was evaluated in primary T lymphocytes obtained from blood of healthy human donors. T lymphocytes were marked permanently with the fluorescent compound Carboxyfluorescein succinimidyl ester (CFSE) and incubated for 3 days at 37° C. on 96-well plates coated with antibody anti-CD3 (10 μg/ml) in the presence of the indicated concentrations of the compounds. Proliferation index was calculated from the intensity of fluorescence of CFSE measured by flow cytometry. As the cells divide they lose CFSE fluorescence because original fluorescence is divided between the daughter cells. This way each division is followed by a dilution of twice the amount of CFSE per cell. So it is possible to calculate the number of divisions. Proliferation index is calculated by dividing the sum of the number of divisions by the calculated number of original parent cells, which have not divided any time. Black square indicates the rate of proliferation of lymphocytes stimulated and not treated with compounds and white square lymphocytes not stimulated with anti-CD3 (FIG. 3).

Example 4

Figure 4:
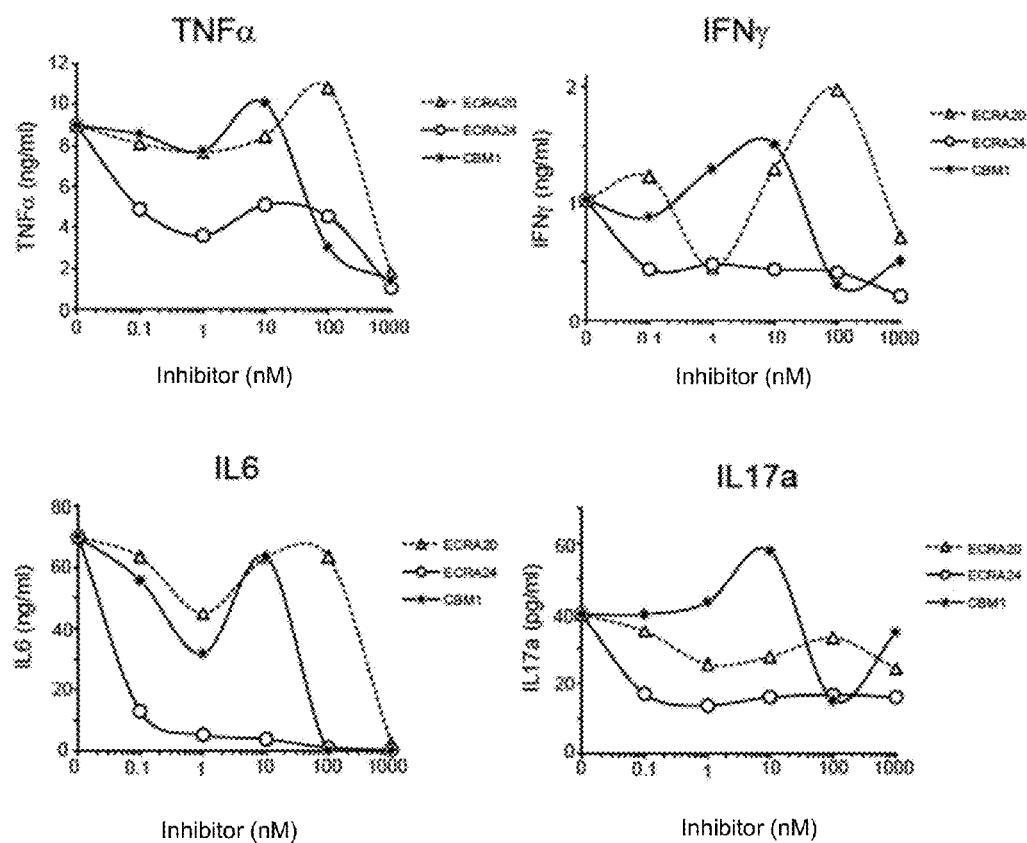
FIG. 4: ECRA20, ECRA24, and CBM-1 compounds inhibit the production of cytokines by T lymphocytes caused by stimulation of the TCR. This shows the inhibitory effect of the compounds on the production of cytokines relevant in inflammation and autoimmune diseases.

Inhibition of the Production of Cytokines by T Lymphocytes Caused by Stimulation of the TCR The effect of the compounds ECRA20, ECRA24, and CBM-1 on the ability of the TCR to induce the secretion of cytokines by T lymphocytes, was evaluated in primary T lymphocytes obtained from blood of healthy human donor. Lymphocytes were stimulated with 10 μg/ml of anti-CD3 plus 1 μg/ml of anti-CD28 in the presence of the indicated quantities of the compounds and the cell supernatants were collected at 24 hours (IFNγ) and 48 hours (TNFα, IL6, and IL17a) to measure the concentration of cytokines secreted in the medium (FIG. 4).

The invention claimed is:
1. A compound of formula I:

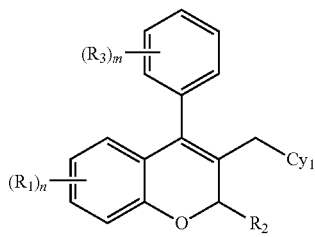

or a salt thereof, where:
each $R_1$ and $R_3$ independently represent hydrogen, $C_{1-4}$alkyl, $C_{2-4}$alkenyl, $C_{2-4}$alkynyl, hydroxyl, $C_{1-4}$alkoxyl, $C_{1-4}$alkoxyC$_{1-4}$alkyl, haloC$_{1-4}$alkyl, hydroxyC$_{1-4}$alkyl, cyanoC$_{1-4}$alkyl, halogen, —CN, or —NO$_2$;
$R_2$ represents hydrogen or $C_{1-4}$alkyl;
$Cy_1$ represents the group:

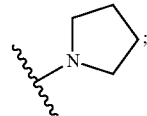

n represents from 0 to 4; and
m represents from 0 to 5.

2. The compound according to claim 1 where each $R_3$ independently represents $C_{1-4}$alkyl, haloC$_{1-4}$alkyl or halogen, preferably haloC$_{1-4}$alkyl or halogen.

3. The compound according to claim 1 where $R_2$ represents hydrogen.

4. The compound according to claim 1 where n represents 0 or 1.

5. The compound according to claim 4 where m represents 1.

6. A pharmaceutical composition comprising a compound of formula I according to claim 1 or a pharmaceutically acceptable salt thereof and one or more pharmaceutically acceptable excipients.

7. A method of treatment of diseases mediated by the TCR-Nck interaction in T lymphocytes in a subject in need thereof which comprises administering to said subject an effective amount of a compound of formula I according to claim 1 or a pharmaceutically acceptable salt thereof.

8. The method according to claim 7 where the disease is selected from rejection of transplants; immune, autoimmune and inflammatory diseases; neurodegenerative diseases; and proliferative diseases.

9. The method according to claim 8 where the disease is selected from rejection of transplants, rheumatoid arthritis, psoriatic arthritis, psoriasis, type I diabetes, complications of diabetes, multiple sclerosis, systemic lupus erythematosus, atopic dermatitis, mast cell-mediated allergic reactions, leukemias, lymphomas and thromboembolic and allergic complications associated with leukemias and lymphomas.

10. A process of preparation of a compound of formula I according to claim 1, comprising:
(a) reacting a compound of formula II with a compound of formula III

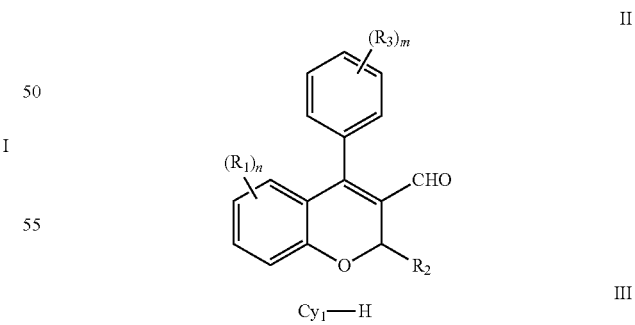

where $R_1$, $R_2$, $R_3$, $Cy_1$, n and m have the meaning described in claim 1; and/or
(b) transform, in one or several stages, a compound of formula I in another compound of formula I.

* * * * *